(12) United States Patent
Shanechi

(10) Patent No.: US 10,675,406 B2
(45) Date of Patent: Jun. 9, 2020

(54) ADAPTIVE BRAIN-MACHINE INTERFACE SYSTEM FOR ANESTHESIA DELIVERY

(71) Applicant: University of Southern California, Los Angeles, CA (US)

(72) Inventor: Maryam M. Shanechi, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 747 days.

(21) Appl. No.: 15/247,911

(22) Filed: Aug. 25, 2016

(65) Prior Publication Data

US 2017/0113002 A1 Apr. 27, 2017

Related U.S. Application Data

(60) Provisional application No. 62/245,910, filed on Oct. 23, 2015.

(51) Int. Cl.
| | |
|---|---|
| *A61M 5/172* | (2006.01) |
| *A61M 5/142* | (2006.01) |
| *G06F 19/00* | (2018.01) |
| *G16H 50/20* | (2018.01) |
| *A61B 5/00* | (2006.01) |
| *A61B 5/0476* | (2006.01) |
| *A61M 5/14* | (2006.01) |

(52) U.S. Cl.
CPC ......... *A61M 5/1723* (2013.01); *A61B 5/4821* (2013.01); *A61M 5/142* (2013.01); *G06F 19/3468* (2013.01); *G16H 50/20* (2018.01); *A61B 5/0476* (2013.01); *A61B 5/4839* (2013.01); *A61M 5/14* (2013.01); *A61M 2005/14208* (2013.01); *A61M 2202/048* (2013.01); *A61M 2205/50* (2013.01); *A61M 2230/10* (2013.01)

(58) Field of Classification Search
CPC .................................................. A61M 5/1723
USPC ......................................................... 703/11
See application file for complete search history.

(56) References Cited

PUBLICATIONS

Agarwal et al., "Comparison of closed loop vs. manual administration of propofol using the Bispectral index in cardiac surgery", Acta Anaesthesiologica Scandinavica, 2009; 53(3):390-397.
Alkire et al., "Toward a unified theory of narcosis: brain imaging evidence for a thalamocortical switch as the neurophysiologic basis of anesthetic-induced unconsciousness", Consciousness and cognition, 2000; 9(3):370-386.
Amzica, "Basic physiology of burst-suppression", Epilepsia, 2009; 50(s12):38-39.
Åström, "Theory and applications of self-tuning regulators. In: Control Theory, Numerical Methods and Computer Systems Modelling", Springer; 1975. p. 669-680.
Åström et al., "Adaptive control", Courier Dover Publications; 2013.
Avidan et al., "Prevention of intraoperative awareness in a high-risk surgical population", New England Journal of Medicine, 2011;365(7):591-600.
Barreiros et al., "A self-tuning generalized predictive power system stabilizer", International Journal of Electrical Power & Energy Systems, 1998; 20(3):213-219.
Bertsekas et al., "Dynamic programming and optimal control", vol. 1. Athena Scientific, Belmont, MA; 1995.
Bickford, "Automatic electroencephalographic control of general anesthesia", Electroencephalography and Clinical Neurophysiology, 1950; 2(1):93-96.
Bickford, "Use of frequency discrimination in the automatic electroencephalographic control of anesthesia (servo-anesthesia)", Electroencephalography and Clinical Neurophysiology, 1951; 3(1):83-86.
Brown et al., "General anesthesia, sleep, and coma", New England Journal of Medicine, vol. 363, No. 27, pp. 2638-2650, 2010.
Camacho et al., "Model predictive control", Springer Science & Business Media; 2013.
Chemali et al., "Burst suppression probability algorithms: state-space methods for tracking EEG burst suppression", Journal of Neural Engineering, 2013; 10(5):056017; 1-20.
Ching et al., "A neurophysiological—metabolic model for burst suppression", Proceedings of the National Academy of Sciences, 2012; 109(8):3095-3100.
Ching et al., "Real-time closed-loop control in a rodent model of medically induced coma using burst suppression", Anesthesiology, 2013; 119(4):848-860.
Clarke et al., "A generalized LQG approach to self-tuning control Part I. Aspects of design", International Journal of Control, 1985; 41(6):1509-1523.

(Continued)

*Primary Examiner* — Jerry Lin
(74) *Attorney, Agent, or Firm* — Michael Best & Friedrich LLP

(57) ABSTRACT

A system for controlling a state of anesthesia of a patient. The system includes a neural sensor configured to be coupled to a patient and generate an output signal indicative of neural activity of the patient; and an electronic processor. The electronic processor is coupled to the neural sensor and to an infusion pump, and is configured to receive the output signal from the neural sensor, estimate a drug concentration of the patient based on a model including a first model parameter, and estimate a second model parameter based on the output signal from the neural sensor. The electronic processor is also configured to update the model for estimating the drug concentration of the patient with the second model parameter, and output control signals to the infusion pump to deliver a drug, the output signals being based on the estimated drug concentration for the patient and estimates of the parameters.

24 Claims, 13 Drawing Sheets

(56) References Cited

PUBLICATIONS

Cotten et al., "Closed-loop continuous infusions of etomidate and etomidate analogs in rats: a comparative study of dosing and the impact on adrenocortical function", Anesthesiology, 2011;115(4):764-773.

De Smet et al., "Estimation of optimal modeling weights for a Bayesian-based closed-loop system for propofol administration using the bispectral index as a controlled variable: a simulation study", Anesthesia & Analgesia, 2007; 105(6):1629-1638.

De Smet et al., "The accuracy and clinical feasibility of a new bayesian-based closed-loop control system for propofol administration using the bispectral index as a controlled variable", Anesthesia & Analgesia, 2008;107(4):1200-1210.

Doyle et al., "Burst suppression or isoelectric encephalogram for cerebral protection: evidence from metabolic suppression studies", British Journal of Anaesthesia, 1999; 83(4):580-584.

Faul et al., "Gaussian process modeling of EEG for the detection of neonatal seizures", Biomedical Engineering, IEEE Transactions on, 2007;54(12):2151-2162.

Forssell et al., "Closed-loop identification revisited", Automatica, 1999; 35(7):1215-1241.

Frenzel et al., "Is the bispectral index appropriate for monitoring the sedation level of mechanically ventilated surgical ICU patients? Intensive care medicine", 2002; 28(2):178-183.

Gajraj et al., "Analysis of the EEG bispectrum, auditory evoked potentials and the EEG power spectrum during repeated transitions from consciousness to unconsciousness", British Journal of Anaesthesia, 1998; 80(1):46-52.

Gill et al., "Can the bispectral index monitor quantify altered level of consciousness in emergency department patients?" Academic emergency medicine, 2003; 10(2):175-179.

Glass, "Automated control of anesthesia ten years later: futuristic novelty or present day reality", Canadian Journal of Anesthesia/Journal Canadien d'anesthesie, 2010; 57(8):715-719,.

Grimble, "Implicit and explicit LQG self-tuning controllers", Automatica, 1984; 20(5):661-669.

Grimble, "Multivariate controllers for LQG self-tuning applications with coloured measurement noise and dynamic cost weighting", International Journal of Systems Science, 1986; 17(4):543-557.

Haddad et al., "Adaptive control for non-negative and compartmental dynamical systems with applications to general anesthesia", International Journal of Adaptive Control and Signal Processing, 2003; 17(3):209-235.

Haddad et al., "Neural network adaptive output feedback control for intensive care unit sedation and intraoperative anesthesia", Neural Networks, IEEE Transactions on, 2007; 18(4):1049-1066.

Hemmerling et al., "A randomized controlled trial demonstrates that a novel closed-loop propofol system performs better hypnosis control than manual administration", Canadian Journal of Anesthesia/Journal canadien d'anesthesie, 2010; 57(8):725-735.

Hong et al., "Self-tuning optimal PI rate controller for end-to-end congestion with LQR approach. In: Managing Traffic Performance in Converged Networks", Springer; 2007, p. 829-840.

Ioannou et al., "Robust adaptive control", Courier Corporation; 2012.

Jalili-Kharaajoo et al., "Genetic algorithm based parameter tuning of adaptive LQR-repetitive controllers with application to uninterruptible power supply systems. In: Innovations in Applied Artificial Intelligence", Springer; 2004, p. 583-593.

Kenny et al., "Closed-loop control of propofol anaesthesia", British Journal of Anaesthesia, 1999;83(2):223-228.

Khalil et al., "Nonlinear systems", vol. 3. Prentice Hall, Upper Saddle River; 2002.

Liberman et al., "A closed-loop anesthetic delivery system for real-time control of burst suppression", Journal of Neural Engineering, 2013; 10(4):046004.

Linkens et al., "Self-adaptive and self-organising control applied to nonlinear multivariable anaesthesia: a comparative model-based study", In: Control Theory and Applications, IEE Proceedings D. vol. 139. IET; 1992, p. 381-394.

Linkens, "Adaptive and intelligent control in anesthesia", Control Systems, IEEE. 1992; 12(6):6-11.

Liu et al., "Closed-loop control of consciousness during lung transplantation: an observational study", Journal of Cardiothoracic and Vascular Anesthesia, 2008; 22(4):611-615, PLOS 33/45.

Liu et al., "Feasibility of closed-loop titration of propofol and remifentanil guided by the spectral M-Entropy monitor", Anesthesiology, vol. 116, No. 2, pp. 286-295, 2012.

Liu et al., "Titration of propofol for anesthetic induction and maintenance guided by the bispectral index: closed-loop versus manual control: a prospective, randomized, multicenter study", Anesthesiology, 2006; 104(4):686-695.

Ljung et al., "System identification", Springer; 1998.

Lu et al., "Relative reliability of the auditory evoked potential and Bispectral Index for monitoring sedation level in surgical intensive care patients", Anaesthesia and intensive care, 2008; 36(4):553-559.

Mager et al., "Diversity of mechanism-based pharmacodynamics models", Drug Metabolism and Disposition, 2003; 31(5):510-518.

Martin-Mateos et al., "Modelling propofol pharmacodynamics using BIS-guided anaesthesia", Anaesthesia, 2013; 68(11):1132-1140.

Mayo et al., "Electroencephalographically controlled anesthesia in abdominal surgery", Journal of the American Medical Association, 1950; 144(13):1081-1083.

Mortier et al., "Closed-loop controlled administration of propofol using bispectral analysis", Anaesthesia, 1998; 53(8):749-754.

Nasraway Jr. et al., "How reliable is the Bispectral Index in critically ill patients? A prospective, comparative, single-blinded observer study*", Critical care medicine, 2002; 30(7):1483-1487.

O'Hara et al., "The use of computers for controlling the delivery of anesthesia", Anesthesiology, 1992; 77(3):563-581.

Park et al., "Bispectral index does not correlate with observer assessment of alertness and sedation scores during 0.5% bupivacaine epidural anesthesia with nitrous oxide sedation", Anesthesia & Analgesia, 2006; 103(2):385-389. PLOS 35/45.

Purdon et al., "Electroencephalogram signatures of loss and recovery of consciousness from propofol", Proceedings of the National Academy of Sciences, 2013; 110(12):E1142-E1151.

Puri et al., "Closed-loop anaesthesia delivery system (CLADS) using bispectral index: a performance assessment study", Anaesthesia and intensive care, 2007; 35(3):357-362.

Rinehart et al., "Closed-Loop Systems in Anesthesia: Is There a Potential for Closed-Loop Fluid Management and Hemodynamic Optimization?" Anesthesia & Analgesia, 2012;114(1):130-143.

Rossetti et al., "Propofol treatment of refractory status epilepticus: a study of 31 episodes", Epilepsia, 2004; 45(7):757-763.

Schnider et al., "The influence of method of administration and covariates on the pharmacokinetics of propofol in adult volunteers", Anesthesiology, 1998; 88(5):1170-1182.

Schwartz et al., "General anesthesia, sleep, and coma", New England Journal of Medicine, 2010; 363(27):2638-2650.

Schwender et al., "Conscious awareness during general anaesthesia: patients' perceptions, emotions, cognition and reactions", British Journal of Anaesthesia, 1998; 80(2):133-139.

Schwilden et al., "Closed-loop feedback control of methohexital anesthesia by quantitative EEG analysis in humans", Anesthesiology, 1987; 67(3):341-347.

Schwilden et al., "Closed-loop feedback control of propofol anaesthesia by quantitative EEG analysis in humans", British Journal of Anaesthesia, 1989; 62(3):290-296.

Schwilden et al., "Closed-loop feedback controlled administration of alfentanil during alfentanil-nitrous oxide anaesthesia", British Journal of Anaesthesia, 1993; 70(4):389-393.

Schwilden et al., "Model-Based Adaptive Control of Volatile Anesthetics by Quantitative EEG. In: Control and Automation in Anaesthesia", Springer; 1995. p. 163-174.

Shafer et al., "Pharmacokinetics and pharmacodynamics of propofol infusions during general anesthesia", Anesthesiology, 1988; 69(3):348-356.

(56) References Cited

PUBLICATIONS

Shanechi et al., "A brain-machine interface for control of medically-induced coma", PLoS computational biology, vol. 9, No. 10, p. e1003284, 2013.

Shanechi et al., "A real-time brain-machine interface combining motor target and trajectory intent using an optimal feedback control design", PloS one, 2013; 8(4):e59049.

Shanechi et al., "Feedback-controlled parallel point process filter for estimation of goal-directed movements from neural signals", Neural Systems and Rehabilitation Engineering, IEEE Transactions on, 2013; 21(1):129-140.

Shanechi et al., "Neural population partitioning and a concurrent brain-machine interface for sequential motor function", Nature neuroscience, 2012;15(12):1715-1722.

Struys et al., "Comparison of closed-loop controlled administration of propofol using Bispectral Index as the controlled variable versus "standard practice" controlled administration", Anesthesiology, 2001; 95(1):6-17.

Truccolo et al., "A point process framework for relating neural spiking activity to spiking history, neural ensemble, and extrinsic covariate effects", Journal of neurophysiology, 2005;93(2):1074-1089.

Varvel et al., "Measuring the predictive performance of computer-controlled infusion pumps", Journal of pharmacokinetics and biopharmaceutics. 1992; 20(1):63-94.

Vijn et al., "IV anaesthesia and EEG burst suppression in rats: bolus injections and closed-loop infusions." British Journal of Anaesthesia, 1998; vol. 81, No. 3, pp. 415-421.

Vishnoi et al., "Adaptive control of closed-circuit anesthesia", Biomedical Engineering, IEEE Transactions on. 1991; 38(1):39-47.

Westover et al., "Robust control of burst suppression for medical coma", Journal of Neural Engineering, 2015; 12(4):046004.

Whitlock et al., "Relationship between bispectral index values and volatile anesthetic concentrations during the maintenance phase of anesthesia in the B-Unaware trial", Anesthesiology, 2011; 115(6):1209, PLOS 37/45.

Yang et al., "An adaptive brain-machine interface algorithm for control of burst suppression in medical coma", in Proc. IEEE Engineering in Medicine and Biology Society Conference (EMBC), Chicago, IL, 2014 (4 pages).

ADAPTIVE BRAIN-MACHINE INTERFACE SYSTEM FOR ANESTHESIA DELIVERY

CROSS-REFERENCE TO RELATED APPLICATIONS

This application is a non-provisional of and claims priority to U.S. Provisional Application No. 62/245,910, filed on Oct. 23, 2015, the entire contents of which are incorporated herein by reference.

BACKGROUND OF THE INVENTION

Control of brain states in patients requiring anesthesia care is a critical topic in modern medicine. E. N. Brown, R. Lydic, and N. D. Schiff, "General anesthesia, sleep, and coma," New England Journal of Medicine, vol. 363, no. 27, pp. 2638-2650, 2010; P. L. Purdon, E. T. Pierce, E. A. Mukamel, M. J. Prerau, J. L. Walsh, K. F. K. Wong, A. F. Salazar-Gomez, P. G. Harrell, A. L. Sampson, A. Cimenser, et al., "Electroencephalogram signatures of loss and recovery of consciousness from propofol," Proceedings of the National Academy of Sciences, vol. 110, no. 12, pp. E1142-E1151, 2013; A. O. Rossetti, M. D. Reichhart, M.-D. Schaller, P.-A. Despland, and J. Bogousslavsky, "Propofol treatment of refractory status epilepticus: a study of 31 episodes," Epilepsia, vol. 45, no. 7, pp. 757-763, 2004; P. Doyle and B. Matta, "Burst suppression or isoelectric encephalogram for cerebral protection: evidence from metabolic suppression studies." British journal of anaesthesia, vol. 83, no. 4, pp. 580-584, 1999. Today the state of anesthesia is induced manually by continuously administering an anesthetic drug, such as propofol. Anesthesiologists or intensive care unit (ICU) staff monitor indirect measures of the brain's anesthetic state, such as heart rate and blood pressure, and in some cases also the brain's activity on the electroencephalogram (EEG). P. L. Purdon, E. T. Pierce, E. A. Mukamel, M. J. Prerau, J. L. Walsh, K. F. K. Wong, A. F. Salazar-Gomez, P. G. Harrell, A. L. Sampson, A. Cimenser, et al., "Electroencephalogram signatures of loss and recovery of consciousness from propofol," Proceedings of the National Academy of Sciences, vol. 110, no. 12, pp. E1142-E1151, 2013. They then manually titrate the anesthetic drug infusion rate to maintain a target anesthetic state.

An alternative approach to manual administration is to define numerically a target level of the brain's anesthetic state, and implement a computer-controlled closed-loop anesthetic delivery (CLAD) system or a brain-machine interface (BMI) that automatically monitors the brain's anesthetic state based on the neural activity and adjusts the drug infusion rate in real time to maintain the specified target level. Such automatic control could lead to more reliable and accurate real-time anesthetic delivery than is realistic to expect using manual administration. M. M. Struys, T. De Smet, L. F. Versichelen, S. Van de Velde, R. Van den Broecke, and E. P. Mortier, "Comparison of closed-loop controlled administration of propofol using bispectral index as the controlled variable versus "standard practice" controlled administration," Anesthesiology, vol. 95, no. 1, pp. 6-17, 2001; J. Agarwal, G. Puri, and P. Mathew, "Comparison of closed loop vs. manual administration of propofol using the bispectral index in cardiac surgery," Acta anaesthesiologica Scandinavica, vol. 53, no. 3, pp. 390-397, 2009; T. De Smet, M. M. Struys, M. M. Neckebroek, K. Van den Hauwe, S. Bonte, and E. P. Mortier, "The accuracy and clinical feasibility of a new bayesian-based closed-loop control system for propofol administration using the bispectral index as a controlled variable," Anesthesia & Analgesia, vol. 107, no. 4, pp. 1200-1210, 2008; T. M. Hemmerling, S. Charabati, C. Zaouter, C. Minardi, and P. A. Mathieu, "A randomized controlled trial demonstrates that a novel closed-loop propofol system performs better hypnosis control than manual administration," Canadian Journal of Anesthesia/Journal canadien d`anesth´esie, vol. 57, no. 8, pp. 725-735, 2010; N. Liu, T. Chazot, A. Genty, A. Landais, A. Restoux, K. McGee, P.-A. Lalo¨ e, B. Trillat, L. Barvais, and M. Fischler, "Titration of propofol for anesthetic induction and maintenance guided by the bispectral index: closed-loop versus manual control: a prospective, randomized, multicenter study." Anesthesiology, vol. 104, no. 4, pp. 686-695, 2006; N. Liu, T. Chazot, B. Trillat, M. Michel-Cherqui, J. Y. Marandon, J.-D. Law-Koune, B. Rives, M. Fischler, F. L. T. Group, et al., "Closed-loop control of consciousness during lung transplantation: an observational study," Journal of cardiothoracic and vascular anesthesia, vol. 22, no. 4, pp. 611-615, 2008. Moreover, an automatic system would result in more efficient use of the anesthesia care personnel. This is especially important in medically-induced coma, also termed medical coma, which needs to be maintained for long periods of hours or days. Hence the focus in our recent work has been on developing a BMI for medically-induced coma in a rodent model. M. M. Shanechi, J. J. Chemali, M. Liberman, K. Solt, and E. N. Brown, "A brain-machine interface for control of medically-induced coma," PLoS computational biology, vol. 9, no. 10, p. e1003284, 2013.

Medically-induced coma is a drug-induced state of profound brain inactivation used after traumatic brain injuries and for treatment of status epilepticus (i.e., uncontrollable seizures). The EEG signal in medical coma, termed burst suppression, consists of bursts of electrical activity alternating with suppression periods. F. Amzica, "Basic physiology of burst-suppression," Epilepsia, vol. 50, no. s12, pp. 38-39, 2009; S. Ching, P. L. Purdon, S. Vijayan, N. J. Kopell, and E. N. Brown, "A neurophysiological-metabolic model for burst suppression," Proceedings of the National Academy of Sciences, vol. 109, no. 8, pp. 3095-3100, 2012. For burst suppression, CLAD systems using non-model based control have been implemented in a rodent model (P. Vijn and J. Sneyd, "Iv anaesthesia and eeg burst suppression in rats: bolus injections and closed-loop infusions." British journal of anaesthesia, vol. 81, no. 3, pp. 415-421, 1998; J. F. Cotten, R. Le Ge, N. Banacos, E. Pejo, S. S. Husain, J. H. Williams, and D. E. Raines, "Closed-loop continuous infusions of etomidate and etomidate analogs in rats: a comparative study of dosing and the impact on adrenocortical function," Anesthesiology, vol. 115, no. 4, p. 764, 2011) that controlled a constant level of burst suppression rather than time-varying levels needed in medical coma.

Model-based CLADs for management of medical coma only appeared recently in our work (M. M. Shanechi, J. J. Chemali, M. Liberman, K. Solt, and E. N. Brown, "A brain-machine interface for control of medically-induced coma," PLoS computational biology, vol. 9, no. 10, p. e1003284, 2013) and in (S. Ching, M. Y. Liberman, J. J. Chemali, M. B. Westover, J. D. Kenny, K. Solt, P. L. Purdon, and E. N. Brown, "Real-time closed-loop control in a rodent model of medically induced coma using burst suppression," Anesthesiology, vol. 119, no. 4, pp. 848-860, 2013.); these CLADs worked by controlling the burst suppression probability (BSP)—taking values in [0;1]—, which is defined as the brain's instantaneous probability of being suppressed and measures the level of burst suppression. M. M. Shanechi, J. J. Chemali, M. Liberman, K. Solt, and E. N. Brown, "A brain-machine interface for control of medically-induced coma," PLoS computational biology, vol. 9, no. 10, p. e1003284, 2013; S. Ching, M. Y. Liberman, J. J. Chemali, M. B. Westover, J. D. Kenny, K. Solt, P. L. Purdon, and E. N. Brown, "Real-time closed-loop control in a rodent model of medically induced coma using burst suppression," Anesthesiology, vol. 119, no. 4, pp. 848-860, 2013; J. Chemali, S. Ching, P. L. Purdon, K. Solt, and E. N. Brown, "Burst suppression probability algorithms: state-space methods for tracking eeg burst suppression," Journal of neural engineering, vol. 10, no. 5, p. 056017, 2013.

The recent CLADs for medical coma have four limiting features that hinder their clinical viability as follows.

(1) Recent CLADs for medical coma require a separate offline system-identification session to be performed before real-time control and treatment can initiate. In this session, a bolus of propofol in the form of a square pulse (M. M. Shanechi, J. J. Chemali, M. Liberman, K. Solt, and E. N. Brown, "A brain-machine interface for control of medically-induced coma," PLoS computational biology, vol. 9, no. 10, p. e1003284, 2013; S. Ching, M. Y. Liberman, J. J. Chemali, M. B. Westover, J. D. Kenny, K. Solt, P. L. Purdon, and E. N. Brown, "Real-time closed-loop control in a rodent model of medically induced coma using burst suppression," Anesthesiology, vol. 119, no. 4, pp. 848-860, 2013) is administered to the subject. Recent simulation studies have replaced this square pulse with a ramp-drop pulse (M. B. Westover, S.-E. Kim, S. Ching, P. L. Purdon, and E. N. Brown, "Robust control of burst suppression for medical coma," Journal of Neural Engineering, vol. 12, no. 4, p. 046004, 2015) that requires as long as 30 min then calculated in this session and used to fit the model parameters. However, such a system-identification session requires a possibly long delay or interruption in treatment, which may not be feasible in the ICU or safe for the patient. Moreover, it may lead to seizure recurrence in status-epilepticus in some patients. M. B. Westover, S.-E. Kim, S. Ching, P. L. Purdon, and E. N. Brown, "Robust control of burst suppression for medical coma," Journal of Neural Engineering, vol. 12, no. 4, p. 046004, 2015.

(2) Biased performance can occur in prior CLADs for medical coma; for example, in our prior rodent experiments (M. M. Shanechi, J. J. Chemali, M. Liberman, K. Solt, and E. N. Brown, "A brain-machine interface for control of medically-induced coma," PLoS computational biology, vol. 9, no. 10, p. e1003284, 2013), while control at some levels was unbiased, it exhibited bias at other levels. This is because these CLADs build parametric models of burst suppression and drug dynamics, but assume that model parameters are time-invariant and not a function of the anesthetic level. However, brain dynamics in response to anesthetics are non-stationary and time-varying and may change as a function of the depth of anesthesia. While incorporating loop-shaping can help with relatively small inter-subject variabilities (M. B. Westover, S.-E. Kim, S. Ching, P. L. Purdon, and E. N. Brown, "Robust control of burst suppression for medical coma," Journal of Neural Engineering, vol. 12, no. 4, p. 046004, 2015), it cannot track the time-varying nature of the biological system.

(3) Prior CLADs for medical coma do not enforce a limit on infusion rate variations at steady state. This may cause over-sensitivity to noise, leading to periodic or unstable operation of the infusion pump as we observed in some of our rodent experiments.

(4) None of the existing CLAD systems provide theoretical guarantees on performance or bias.

(5) Prior CLADs in the anesthesia field have not been generalizable to different anesthetic states. We develop the novel adaptive system to be generalizable to other states of anesthesia in addition to medical coma. We accomplish generalizability by offering a systematic scheme to build parametric models including stochastic models, pharmacokinetic models, pharmacodynamics models.

SUMMARY OF THE INVENTION

The above limitations are addressed by embodiments of an adaptive controller for medical coma as described below. To resolve the first two limitations, a time-varying parametric drug dynamics models was built, and novel adaptive estimation and feedback control algorithms were designed. These novel components form an adaptive system that can operate without any initial knowledge of the model parameter values, thus removing the need for a separate system-identification session. Moreover, the adaptive system tracks time-varying dynamics and non-stationarity, thus removing the observed bias at all levels. To resolve the third limitation, i.e., to ensure low steady-state rate variability, in the feedback-controller design the large changes between adjacent infusion rates at steady state were explicitly penalized. Finally, to resolve the last limitation, theoretical analysis was performed to demonstrate, interestingly, that estimating merely a ratio of model parameters without their exact values is sufficient for precise adaptive control under non-stationary time-varying parameters. Various other states of anesthesia could also benefit from automatic CLAD control.

The present invention relates to automated control of anesthesia delivery to a patient.

In one embodiment, the invention provides a method of determining a drug infusion rate. The method includes receiving a target anesthetic state, receiving neural electrical signals from a patient's brain, and determining, based on the neural electrical signals, a value of a neural signature. The neural signature is associated with the target anesthetic state. The method also includes estimating a brain drug concentration and a model parameter for a current time, and accessing a previously estimated brain drug concentration and model parameter for the current time. The method further includes calculating, based on the previously estimated brain drug concentration and model parameter, an improved estimate of the brain drug concentration and an improved estimate of the model parameter for the current time, and determining, based on the improved estimate of the model parameter and the improved estimate of the brain drug concentration, an optimal drug infusion rate.

In some embodiments, receiving a target anesthetic state includes one of a group consisting of receiving a burst suppression state under medical coma, and receiving an unconsciousness state under general anesthesia. In some embodiments, the method also includes determining, based on the target anesthetic state, a target brain drug concentration. Additionally, in some or other embodiments, the method also includes generating an estimate of the brain drug concentration and the model parameter for a future time.

In other embodiments, the method also includes determining a cost function based on the improved estimate of the model parameter and the target anesthetic state, and wherein determining the optimal infusion rate includes minimizing the cost function to determine the optimal infusion rate.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Typically, a state of anesthesia is induced manually, with an anesthesiologist or other intensive care unit staff manually titrating an anesthetic drug infusion rate. The anesthesiologist or other medical staff determines an appropriate drug infusion rate by monitoring the patient's brain activity on the electroencephalogram (EEG) visually. Some anesthesiologists and/or staff members may alternatively or additionally use indirect measures of unconsciousness (e.g., heart rate, muscle tone, blood pressure, etc.) to determine the appropriate drug infusion rate for the patient.

In some instances, the anesthesiologist and/or medical staff may utilize a computer-controlled closed-loop anesthetic delivery system. The anesthetic delivery systems use a static (i.e., non-changing, non-adaptive, or permanent) model for determining the drug infusion rate. The brain's physiological response, however, changes based on the anesthetic state of the patient and the drug infusion rate. Therefore, these permanent models may not accurately represent an infusion rate to maintain the patient at the target anesthetic state.

Additionally, these anesthetic delivery systems typically require a system identification procedure to be performed prior to administering the anesthesia. The identification procedure serves to provide the system with a basis (e.g., normal) brain activity signals to determine parameter values for the static model. This identification procedure, however, requires additional time and resources.

Figure 1:
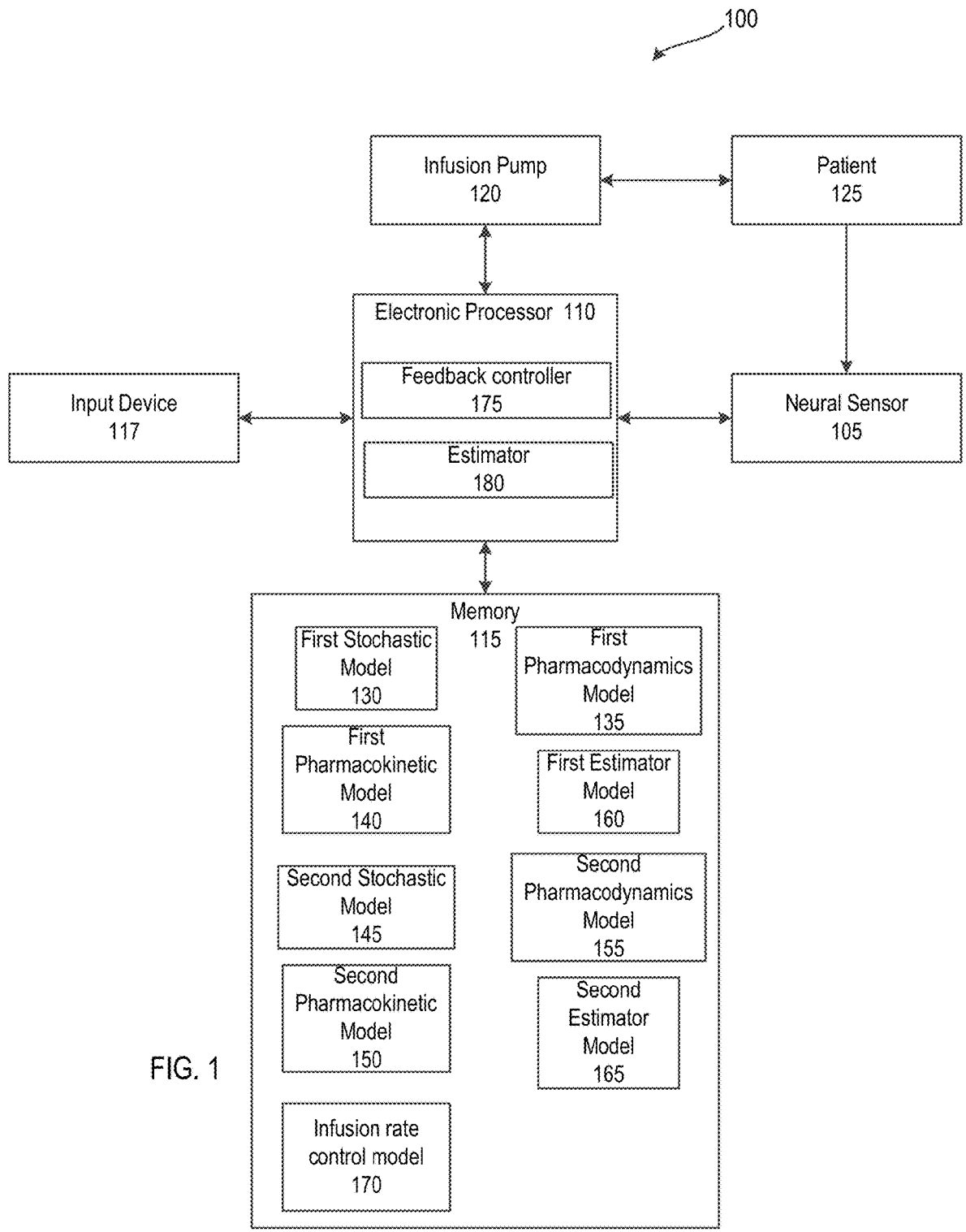
FIG. 1 illustrates a block diagram of an adaptive and generalizable anesthetic drug delivery system according to an embodiment of the invention.

FIG. 1 is a block diagram of an adaptive and generalizable anesthetic drug delivery system 100. As discussed in more detail below, unlike the anesthetic delivery systems that use a static model, the adaptive and generalizable anesthetic drug delivery system 100 adapts the model parameters such that an accurate infusion rate may be calculated under different anesthetic states and as the brain's response to the anesthetic drug changes under an anesthetic state. As shown in FIG. 1, the drug delivery system 100 includes a neural sensor 105, an electronic processor 110, a memory 115, and an infusion pump 120. The neural sensor 105 includes, for example, electrodes that are secured to a patient 125 and/or voltage sensors to detect the neural electrical signals sensed by the electrodes. The electrodes generate output signals indicative of the brain activity of the patient. In some embodiments, the neural sensor 105 includes an electroencephalogram machine (EEG machine) as well as the electrodes. The electroencephalogram machine may provide, for example, some processing (e.g., filtering) of the electrical signals output from the electrodes and may provide visualization of the output signals from the electrodes.

The infusion pump 120 is also coupled to the patient 125 via, for example, a delivery tool (not shown). The delivery tool may be, for example, a needle (e.g., such as in an intravenous system) or an oxygen mask. The delivery tool may include a different tool that is used to deliver an agent or a chemical to the patient 125. The infusion pump 120 is coupled to the delivery tool to deliver a drug (e.g., an anesthetic) to the patient 125 at an infusion rate. The infusion pump 120 is a variable speed pump. In other embodiments, the infusion pump 120 may be a single speed pump.

The input interface 117 is coupled to the electronic processor 100. In some embodiments, the input interface 117 includes a plurality of actuators that receive user inputs. For example, the input interface 117 may include a device having a touchscreen, or the input device may include a keyboard, or another device having a set of actuators (e.g., buttons, rotary switches, and the like). The input interface 117 may include, additionally or alternatively, a physical communication port (e.g., USB port, RS232 port, etc.) or a wireless interface (e.g., Wi-Fi, WLAN, Bluetooth®, etc.).

The memory 115 stores a set of models accessed by the electronic processor 110. In some embodiment, the memory 115 stores a plurality of models accessed by the electronic processor 100 to monitor the same anesthetic state as well as different sets of models to monitor different anesthetic states. For example, the memory 115 may store a first stochastic model 130, a first pharmacodynamic model 135, a first pharmacokinetic model 140, a second stochastic model 145, a second pharmacodynamic model 150, and a second pharmacokinetic model 155. The first stochastic model 130, the first pharmacodynamic model 135, and the first pharmacokinetic model 140 are accessed by the electronic processor 110 when the patient is to remain in a first anesthetic state. On the other hand, the second stochastic model 145, the second pharmacodynamic model 150, and the second pharmacokinetic model 155 are accessed by the electronic processor 110 when the patient is to remain in a second anesthetic state, different from the first anesthetic state. In some embodiments, each set of corresponding models are used to generate an estimator model. The memory 115 may then, in some embodiments, only store the estimator model without storing the models used to generate the estimator model. For example, a first estimator model 160 may be based on the first stochastic model 130, the first pharmacodynamic model 135, and the first pharmacokinetic model 140, and accessed by the electronic processor 110 when the patient is to remain in a first anesthetic state. A second estimator model 165 may be based on the second stochastic model 145, the second pharmacodynamic model 150, and the second pharmacokinetic model 155, and accessed by the electronic processor 110 when the patient is to remain in a second anesthetic state. The stochastic models 130, 145, the pharmacodynamic models 135, 150, and the pharmacokinetic models 140, 155 are referred to as parametric models. The parametric models describe the relationships between the output signals from the neural sensor 105, drug concentrations of the patient (i.e., how much drug or anesthetic is present inside the patient), and the infusion rate at which the drug is delivered. These parametric models are then used to generate the estimator models accessed by the electronic processor 110.

The stochastic models 130, 145 describe the quantitative relationship between the measured output signals from the neural sensor 105 and a neural signature that quantifies an anesthetic state of the patient. Each anesthetic state is associated with a particular type and value of a neural signature. In other words, the neural signature is a quantitative measure of the anesthetic state. For example, medically-induced coma is a drug-induced state of profound brain inactivation. Medically-induced coma is sometimes used after traumatic brain injuries and/or for treatment of status epilepticus (i.e., uncontrollable seizures). When a patient is under medically-induced coma, the neural sensor 105 generates an electrical output termed burst suppression. Burst suppression (e.g., the output from the neural sensor 105) consists of bursts of electrical activity alternating with suppression periods. These bursts of electrical activity are pre-processed, for example, by the electronic processor 110 or by another component of the drug delivery system 100, to generate a binary time series. The binary time series is then processed according to a stochastic model (e.g., the first stochastic model 130) to provide a burst suppression probability, the neural signature for medically-induced coma. Different values of the burst suppression probability are indicative of different anesthetic states under a medically-induced coma.

Unconsciousness under general anesthesia is a different type of anesthetic state and therefore utilizes a different stochastic model than medically-induced coma. General anesthesia is a drug-induced anesthetic state widely used during surgery. While a patient is under general anesthesia, a level of unconsciousness of the patient is monitored and controlled. Different types of neural signatures (and therefore different stochastic models) may be used to quantify and monitor the level of unconsciousness under general anesthesia. For example, an electroencephalogram (EEG) bispectral index (BIS), a spectrum median frequency, M-entropy, and/or auditory evoked potentials (AEP) all provide quantitative measures of the level of unconsciousness of a patient under general anesthesia. With respect to the spectrum median frequency, the output signals from the neural sensor 105 are pre-processed, for example, by the electronic processor 110, to generate a time-varying spectra, i.e., the spectrogram of EEG. The spectogram is then processed according to a stochastic model (e.g., the second stochastic model 145) to provide a median frequency, the neural signature for monitoring a level of unconsciousness under general anesthesia. Different values of the median frequency are indicative of different anesthetic states under general anesthesia.

Since different neural signatures may be used to monitor the anesthetic state of a patient, the specific stochastic model 130, 145 for each anesthetic state may be different. However, the stochastic models still follow a general construction that ensures the accuracy of the anesthesia delivery system 100. The construction of the stochastic model 130, 145 is based on the modeling of the output signals $y_t$ from the neural sensor 105, as a non-stationary stochastic process, whose probability density function (PDF) encodes the neural signature $s_t$ as outlined below in Equation 1:

$$p(y_t|s_t) = h(y_t, s_t) \qquad \text{Equation 1}$$

where $y_t$ corresponds to the output signals from the neural sensor 105 (pre-processed by the electronic processor 110 or other component), $s_t$ corresponds to the neural signature, and $h(y_t, s_t)$ is a multivariable function that represents the probability density function of $y_t$.

As recognized by a person of ordinary skill in the art, the particular multivariable function used as $h(y_t, s_t)$ may vary, which provides for the different types of neural signatures that may be used to monitor the anesthetic state of a patient. However, to ensure that the anesthesia delivery system 100 can remain accurate and adaptable even when used with various types of anesthetic states, the multivariable function satisfies various constraints. The constraints include, for example, that the multivariable function $h(y_t, s_t)$ is a scalar function with two scalar arguments, is a probability function distribution with respect to $y_t$, is twice differentiable with respect to $s_t$. Additionally, the partial derivative of the $h(y_t, s_t)$ with respect to $s_t$, when set equal to zero (e.g., $$d(y, s) = \frac{\partial}{\partial s} \log h(y, s) = 0),$$

has a unique solution for $s_t$ as $s = m(y)$. The second partial derivative of $h(y_t, s_t)$ evaluated at $s_t = m(y)$ is less than zero for all of the possible observations by the neural sensor 105 (e.g., $$\Psi(y) = \left[ \frac{\partial^2}{\partial s^2} \log h(y, s) \right]_{s=m(y)} < 0, \, \forall y \in \mathcal{O},$$

where $\mathcal{O}$ is the set containing all possible observations. Finally, the conditional mean function $\bar{y}(s) = \int_{-\infty}^{+\infty} u p(u|s) du$ satisfies $[m(y)]_{y=\bar{y}(s)} = s$, $\forall s \in \mathcal{P}$, where $\mathcal{P}$ denotes all feasible values of the neural signature. Such constraints on the stochastic models 130, 145 allow the anesthesia delivery system 100 to be adaptable for various anesthetic states and neural signatures, so long as the stochastic models used satisfy the above constraints.

The pharmacodynamic models 135, 150 describe the relationship between drug concentration of a patient and the value of the neural signature. In other words, the pharmacodynamic models 135, 150 describes the relationship between the drug concentration of a patient and the pharmacological effects of drugs. The pharmacodynamic response is defined by the neural signature $s_t$. Therefore, the pharmacodynamic models 135, 150 relate the instantaneous value $s_t$ of the neural signature with the instantaneous drug concentration in the brain $x_e(t)$ as illustrated in Equation 2 below:

$$s_t = \bar{s}(x_e(t)) \qquad \text{Equation 2}$$

Because the drug concentration in the brain is always non-negative, $\bar{s}$ is a scalar function with a non-negative scalar argument. The pharmacodynamic model quantifies $x_e(t)$, which is a virtual measure of the actual brain's drug concentration obtained through requantification of the neural signature $s_t$. In order to ensure the adaptability of the anesthetic drug delivery control 110 for various anesthetic states, $\bar{s}(.)$ satisfies two constraints. First, $\bar{s}(x_e(t))$ is twice differentiable with respect to the drug concentration in the brain $x_e(t)$ and $\bar{s}(x_e(t))$ is an invertible function of $x_e(t)$.

Finally, the pharmacokinetic models 140, 155 describe the effect of the drug infusion rate on the drug concentration. The pharmacokinetic models 140, 155 is a two-compartment time-varying model in which one compartment represents the central plasma of the patient and the other compartment represents the brain of the patient. Therefore, the two-compartment pharmacokinetic model 140, 155 includes both a measure of the central plasma drug concentration at time t, expressed as $x_c(t)$ (mg), and a brain drug concentration at time t, expressed as $x_e(t)$. In the illustrated embodiment, the pharmacokinetic models 140, 155 are discrete time-varying two-compartment state-space models defined by Equation 3 below.

$$x_t = A_{t-1} x_{t-1} + B u_{t-1} \qquad \text{Equation 3}$$

Where $$A_t = \begin{bmatrix} 1 - \Delta(\theta_1(t) + \theta_3(t)) & \Delta\theta_2(t) \\ \Delta\theta_1(t) & 1 - \Delta\theta_2(t) \end{bmatrix}, B = \begin{bmatrix} \Delta \\ 0 \end{bmatrix}$$

$$x_t = [x_c(t), x_e(t)]'$$

The control signal u(t) represents the instantaneous infusion rate.

As shown in Equation 3, the pharmacokinetic model 145 includes model parameters $\theta_1(t), \theta_2(t), \theta_3(t)$ which represent the drug flow rate from the central plasma into the brain of the patient, the drug flow rate from the brain back to the central plasma of the patient, and the elimination rate of the drug, respectively. The model parameters are expressed in Hertz and are modeled as unknown and time-varying. Therefore, the time-varying response of the drug dynamics to external and internal factors may be summarized by these model parameters. As explained in more detail below, these parameters are continuously estimated and updated by the electronic processor 110.

The stochastic models 130, 145, the pharmacodynamic models 135, 150, and the pharmacokinetic models 140, 155 are used together to construct an estimator model (e.g., estimator models 160, 165). The estimator models 160, 165 include the mathematical relationships used to analyze the output signals from the neural sensor 105, and estimate a brain drug concentration, as well as the parameters $\theta_1(t), \theta_2(t), \theta_3(t)$. The estimator models 160, 165 are recursive Bayesian estimators that receive the pre-processed output signals from the neural sensors 105 as inputs and output an estimate of the drug concentration of the patient and estimates for each of the parameters $\theta_1(t), \theta_2(t), \theta_3(t)$. The estimator models 135, 150 represent the estimate of drug concentration of the patient and the estimate of the model parameters with an augmented five-dimensional state as illustrated below in Equation 4.

$$\bar{x}_t = [x_c(t), x_e(t), \theta_1(t), \theta_2(t), \theta_3(t)]' \qquad \text{Equation 4}$$

Since all components of the augmented matrix $x_c(t), x_e(t), \theta_1(t), \theta_2(t), \theta_3(t)$ are positive, the estimator models 160, 165 estimate $z_t = \log(\bar{x}_t) = [z_c(t), z_e(t), z_1(t), z_2(t), z_3(t)]'$. The estimate of $z_t$ is then used to find $\bar{x}_t$ as $\bar{x}_t = \exp(z_t)$.

The estimator models 160, 165 each include a prior model and an observation model. The prior model describes a relationship between a drug concentration of the patient and an infusion rate of the drug. In other words, the prior model describes how a quantity of delivered drug affects the drug concentration of the patient. The prior model uses the pharmacokinetic model to describe such a relationship. As such, the prior model is defined by Equation 5 below:

$$z_t = \log\left(\begin{bmatrix} A_{t-1} & 0 \\ 0 & I_3 \end{bmatrix} \exp(z_{t-1}) + \begin{bmatrix} B \\ 0 \end{bmatrix} u_{t-1}\right) + w_{t-1} \triangleq$$

$$f(z_{t-1}, u_{t-1}) + w_{t-1} \qquad \text{Equation 5}$$

where $I_3$ denotes a 3×3 identity matrix, and $w_t$ is additive Gaussian noise with mean 0 and covariance matrix Q. Including the noise term in the prior model enables the estimation models 160, 165 to account for non-stationarity, time-variation, noise, and model mismatch. Therefore, the prior model considers noise and modeling error. As shown by Equation 5, the prior model uses previously estimated parameters $\theta_1(t-1), \theta_2(t-1), \theta_3(t-1)$ (included in $A_{t-1}$) and a previously administered infusion rate $u_{t-1}$ to determine the current (or present) drug concentration of the patient at time t and estimate updated parameters $\theta_1(t), \theta_2(t), \theta_3(t)$ to be used in the next analysis cycle.

The observation model relates the drug concentration of the patient with the pre-processed output signals from the neural sensor 105. The observation model uses the stochastic models 130, 145 and the pharmacodynamic models 135, 150 to describe the relationship between the drug concentration of the patient and the pre-processed output signals from the neural sensor 105. The observation model is defined by Equation 6 below:

$$p(y_t | z_t) = h(y_t, s_t) = h(y_t, \bar{s}(x_e(t))) = h(y_t, \tilde{s}(z_e(t))), \text{ where}$$
$$\tilde{s}(z) = \bar{s}(e^z) \qquad \text{Equation 6}$$

The prior model and the observation model are combined to define the estimator models 160, 165 such that the general solutions may be customized to monitor different types of anesthetic states. Combination of the prior model and the observation model yields the following general relationships for the estimator models 160, 165:

$$z_{t|t-1} = f(z_{t-1|t-1}, u_{t-1}) \qquad \text{Equation 7}$$

$$W_{t|t-1} = F_{t-1} W_{t-1|t-1} F'_{t-1} + Q \qquad \text{Equation 8}$$

$$z_{t|t} = z_{t|t-1} + W_{t|t}[0, g(y_t, s_t), 0, 0, 0]'_{s_t = \tilde{s}(z_e(t|t-1))} \qquad \text{Equation 9}$$

$$W_{t|t}^{-1} = W_{t|t-1}^{-1} + \begin{bmatrix} \begin{pmatrix} 0 & 0 \\ 0 & q(y_t, s_t) \end{pmatrix} & 0_{2\times 3} \\ 0_{3\times 2} & 0_{3\times 3} \end{bmatrix}_{s_t = \tilde{s}(z_e(t|t-1))} \qquad \text{Equation 10}$$

where $0_{3\times 2}$ is a 3 by 2 zero matrix, $0_{2\times 3}$ is a 2 by 3 zero matrix, $0_{3\times 3}$ is a 3 by 3 zero matrix and where $$F = \left[\frac{\partial f}{\partial z}\right]_{z_{t-1|t-1}} \qquad \text{Equation 11}$$

$$g(y_t, s_t) = \alpha_t \frac{\partial}{\partial s_t} \log h(y_t, s_t), \qquad \text{Equation 12}$$

$$\alpha_t = \frac{\partial \bar{s}(z_e(t))}{\partial z_e(t)} \qquad \text{Equation 13}$$

$$q(y_t, s_t) = -\frac{\beta_t}{\alpha_t} g(y_t, s_t) - \alpha_t^2 \frac{\partial^2}{\partial s_t^2} \log h(y_t, s_t) \qquad \text{Equation 14}$$

$$\beta_t = \frac{\partial \bar{s}(z_e(t))}{\partial z_e(t)^2} \qquad \text{Equation 15}$$

As shown by Equations 7-15, the estimator models 160, 165 rely on only the parametric models described earlier and the pre-processed output signals from the neural sensors 150 to generate estimates of the central plasma drug concentration of the patient, the brain drug concentration of the patient, and the parameters $\theta_1(t)$, $\theta_2(t)$, $\theta_3(t)$. In general, the estimator models 160, 165 access stored parameters $\theta_1(t-1)$, $\theta_2(t-1)$, $\theta_3(t-1)$ from a previous time and estimates for the drug concentration of a patient from the previous time. The estimator models then calculate current values for the parameters $\theta_1(t)$, $\theta_2(t)$, $\theta_3(t)$ and calculates current values for the drug concentrations of a patient at the current time. It is noted that because different anesthetic states are monitored using different stochastic models 130, 145 and different pharmacodynamic models 135, 150, the estimator models 160, 165 used to monitor different anesthetic states are defined by different implementations of the relationships described above. As discussed above, each instance of the estimator models 160, 165 may be stored in memory 115 for access by the electronic processor 110 thereby enabling monitoring of different types of anesthetic states.

In one embodiment, the first stochastic model 130, the first pharmacodynamic model 135, and the first pharmacokinetic model 140 are used to generate the first estimator model 160. The first estimator model 160 is used to control and monitor burst suppression in a medically-induced coma. The first stochastic model 130 assumes a binomial distribution for the number of suppressions $y_t$ in a time interval $\Delta$ with at most N suppressions. The first stochastic model 130 is defined by the following Equation 16:

$$p(y_t | s_t) = \binom{N}{y_t} s_t^{y_t}(1-s_t)^{N-y_t} \qquad \text{Equation 16}$$

The first pharmacodynamic model 135 relates the burst suppression probability with the brain drug concentration using a hyperbolic function, which yields Equation 17 describing the first pharmacodynamic model 135:

$$\bar{s}(x) = \frac{1-e^{-x}}{1+e^{-x}} \qquad \text{Equation 17}$$

Using the model above, the target brain's drug concentration can be derived as:

$$x^* = \log\left(\frac{1+s^+}{1-s^+}\right).$$

The first pharmacokinetic model 140 remains as shown in Equation 3. The first stochastic model 130, the first pharmacodynamic model 135, and the first pharmacokinetic model 140 are combined to generate the first estimator model 160. The first estimator model 160 has a similar construction as that shown in Equations 7-10, however, the specific construction of the variables used changes due to changes in the first stochastic model 130 and the first pharmacodynamic model 135. The first estimator model 160 is therefore defined by the following Equations 18-21:

$$q(y_t, s_t) = \alpha_t \frac{y_t - Ns_t}{s_t(1-s_t)} \qquad \text{Equation 18}$$

$$\alpha_t = \frac{x_e(t)e^{x_e(t)}}{(1+e^{x_e(t)})}(1-s_t) \qquad \text{Equation 19}$$

$$q(y_t, s_t) = -\beta_t \frac{y_t - Ns_t}{s_t(1-s_t)} + \alpha_t^2 \frac{Ns_t^2 + (1-2s_t)y_t}{s_t^2(1-s_t)^2} \qquad \text{Equation 20}$$

$$\beta_t = \alpha_t[1 + x_e(t) - (1-s_t)x_e(t)e^{x_e(t)}] \qquad \text{Equation 21}$$

The electronic processor 110 therefore accesses the first estimator model 160 when monitoring a patient under medically-induced coma. The second stochastic model 145, the second pharmacodynamic model 150, and the second pharmacokinetic model 155 are used to generate the second estimator model 165. The second estimator model 165 is used to control the level of unconsciousness under general anesthesia. The second stochastic model 145 assumes a Gaussian stochastic model such that the second stochastic model 145 is defined by Equation 22:

$$p(y_t | s_t) = \frac{1}{\sqrt{2\pi\sigma}} \exp\left(-\frac{1}{2\sigma^2}(y_t - s_t)^2\right) \qquad \text{Equation 22}$$

The second pharmacodynamic model 150 then relates the median frequency with the brain drug concentration using a sigmoid inhibitory model, which yields Equation 23 to describe the second pharmacodynamic model 150:

$$\bar{s}(x) = E_0 - E_{max} \frac{x^\gamma}{c_0^\gamma + x^\gamma} \qquad \text{Equation 23}$$

In Equation 23, $E_0$ is a baseline median frequency value (e.g., the median frequency value when no anesthetic drug is administered), $E_{max}$ is a maximum decrease from full consciousness to full unconsciousness, $c_0$ is the concentration in the brain at half maximal effect, and $\gamma$ describes the steepness of the concentration-response curve. Using this model, the target brain drug concentration can be described as:

$$x^* = c_0\left(\frac{E_0 - s^*}{E_{max} + s^* - E_0}\right)^{\frac{1}{\gamma}}.$$

The second pharmacokinetic model 155 remain as shown in Equation 3. The second stochastic model 145, the second pharmacodynamic model 150, and the second pharmacokinetic model 155 are combined to generate the second estimator model 165. The second estimator model 165 has a similar construction as that shown in Equations 7-10, however, the specific construction of the variables used changes due to changes in the second stochastic model 145 and the second pharmacodynamic model 150. The second estimator model 165 is defined by the following Equations 24-27:

$$g(y_t, s_t) = \frac{\alpha_t}{\sigma^2}(y_t - s_t) \qquad \text{Equation 24}$$

$$\alpha_t = -c_0^\gamma \gamma E_{max} \frac{e^{\gamma z_e(t)}}{(c_0^\gamma + e^{\gamma z_e(t)})^2} \qquad \text{Equation 25}$$

$$q(y_t, s_t) = -\frac{\beta_t}{\sigma^2}(y_t - s_t) + \frac{\alpha_t^2}{\sigma^2} \qquad \text{Equation 26}$$

$$\beta_t = -c_0^\gamma \gamma^2 E_{max} \frac{e^{\gamma z_e(t)}(c_0^\gamma - e^{\gamma z_e(t)})}{(c_0^\gamma + e^{\gamma z_e(t)})^3} \qquad \text{Equation 27}$$

The electronic processor 110 accesses the second estimator model 165 when monitoring a patient under general anesthesia.

Additionally, the memory 115 also stores an infusion rate control model 170. The electronic processor 110 accesses the infusion rate control model 170 to determine an infusion rate at which the anesthetic drug is to be administered to the patient. The infusion rate control model 170 is described in more detail below with respect to Equations 28 and 30. The infusion rate control model 170, unlike the stochastic models 130, 145, the pharmacodynamic models 135, 150, and the pharmacokinetic models 140, 155, does not change based on the target anesthetic state. Rather, the same infusion rate control model 170 is used to determine the infusion rate regardless of the target anesthetic state.

In some embodiments, the memory 115 stores more estimator models allowing the anesthesia delivery system 100 to monitor a plurality of anesthetic states, instead of a single anesthetic state. Additionally, even if the memory 115 does not store more estimator models, another estimator model may be derived to monitor another anesthetic state (e.g., based on stochastic models and pharmacodynamic models that describe the additional anesthetic state). The new estimator model may then be loaded to the memory 115 to be accessed by the electronic processor 110. In this manner, the anesthesia delivery system 100 provides a straightforward method for deriving different estimator models and using the estimator models to control the infusion rate of an anesthetic drug instead of designing a separate and new system to control the infusion rate of an anesthetic drug.

The electronic processor 110 is coupled to the neural sensor 105 (and to any components performing pre-processing of the output signals from the neural sensor 105), the infusion pump 120, the input device 117, and the memory 115. The electronic processor 110 includes a feedback controller 175 and a recursive estimator 180. The feedback controller 175 and the recursive estimator 180 are in communication with each other and work together to determine an infusion rate at which to administer the anesthetic drug to the patient. In particular, the recursive estimator 180 accesses the stochastic models 130, 145, the pharmacodynamic models 135, 150, the pharmacokinetic models 140, 155, and the estimator models 160, 165 to estimate a current drug concentration of the patient and the model parameters. The feedback controller 175 then receives the estimates of the current drug concentration of the patient and the model parameters and accesses the infusion rate control model 170 to determine an appropriate infusion rate of the anesthetic drug to maintain the patient at the target anesthetic state and control the infusion pump 120 to provide the drug (e.g., anesthetic) at the estimated infusion rate. In some embodiments, the electronic processor 110 may not be divided into these two separate components, but may instead operate as a single unit.

Figure 2:
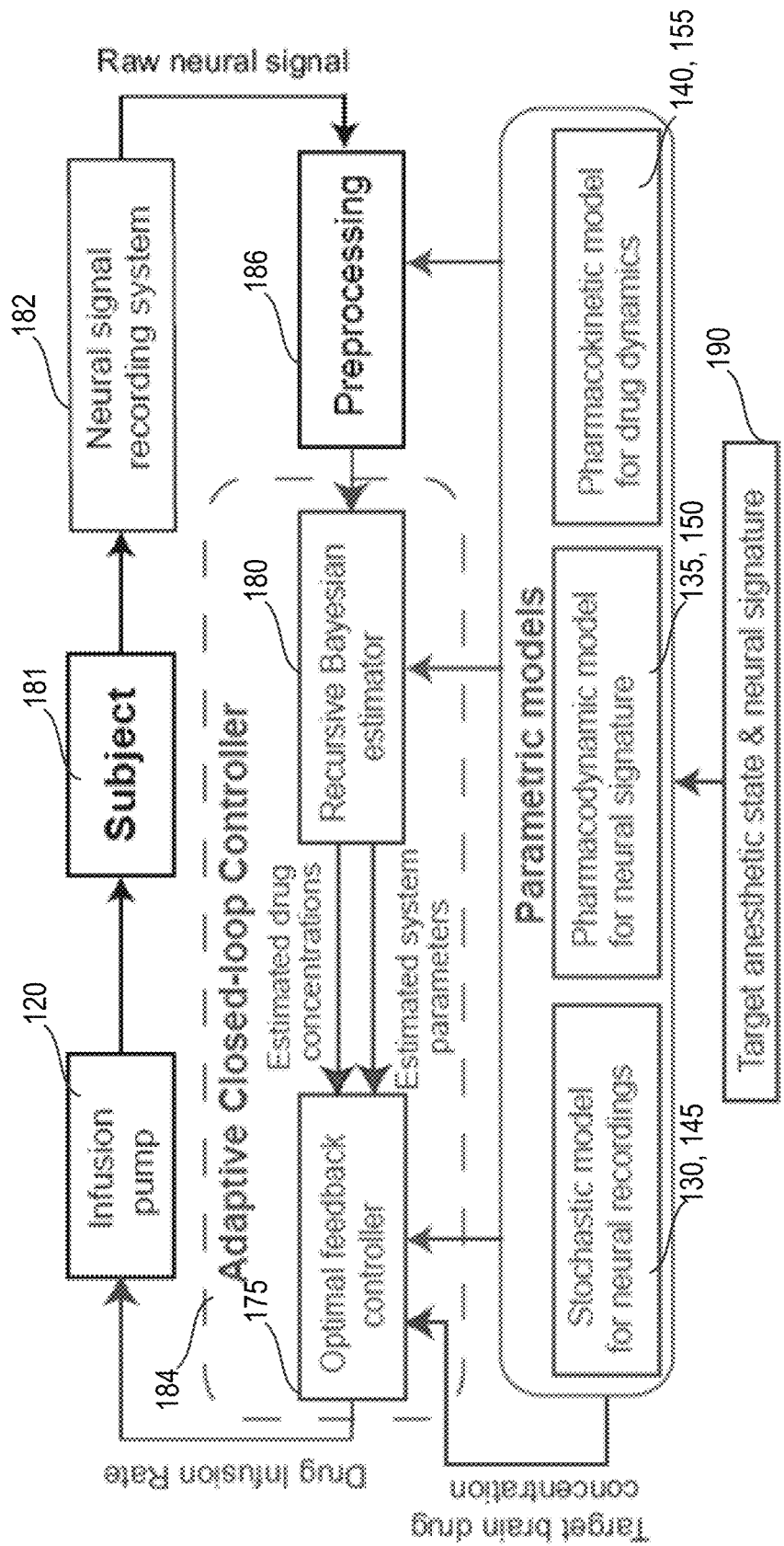
FIG. 2 illustrates a schematic diagram of the adaptive and generalizable anesthetic drug delivery system of FIG. 1.

FIG. 2 illustrates a schematic diagram of the anesthesia delivery system 100 showing more particular connections between the components of the anesthesia delivery system 100. FIG. 2 illustrates a subject 181 receiving the anesthetic drug (similar to the patient 125 shown in FIG. 1), a neural signal recording system 182, an adaptive closed-loop controller 184, the infusion pump 120, and parametric models 130-155. The neural signal recording system 182 may include the electrodes described with reference to the neural sensor 105 and may additionally include other hardware and software components that process the neural signals recorded from the patient. The adaptive closed-loop controller 184 includes the feedback controller 175 and the estimator 180 described with respect to FIG. 1. FIG. 2 also illustrates a preprocessing block 186, a system identification block 188, and a target anesthetic state and neural signature block 190. The components of FIG. 2 will be referred to in the description of the operation of the anesthesia delivery system 100 in FIGS. 3-6.

Figure 3:
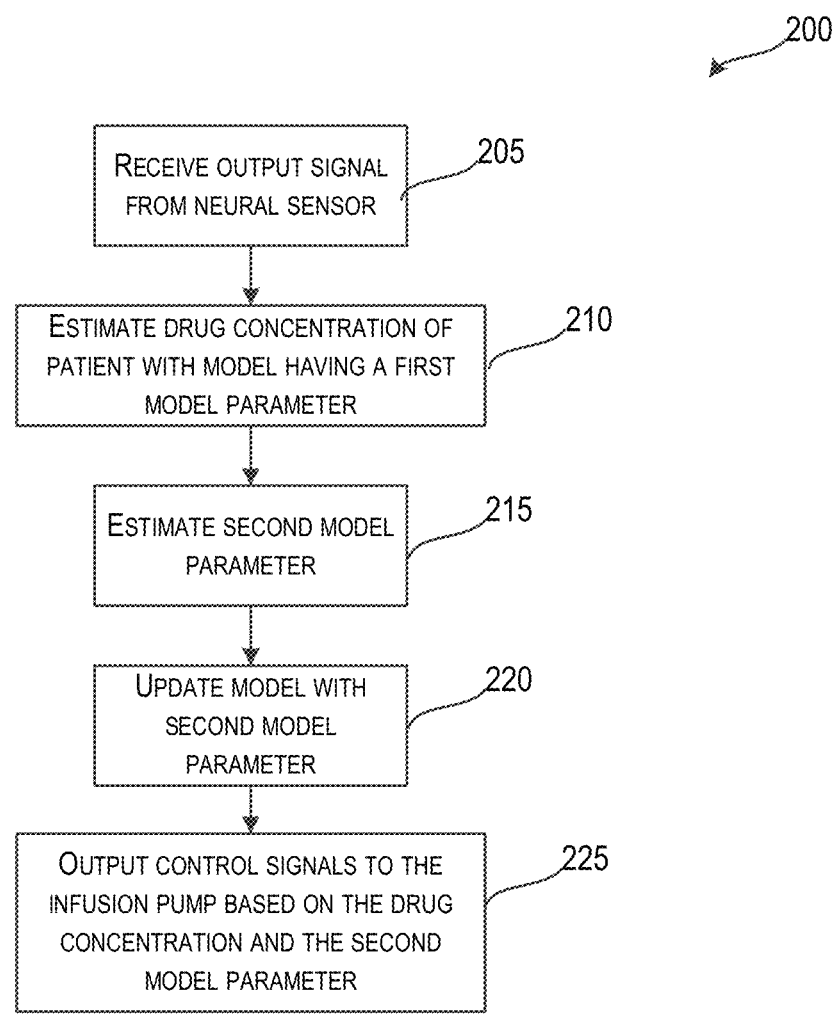
FIG. 3 is a flowchart illustrating a method of operating the anesthesia delivery system of FIG. 1 according to an embodiment of the invention.

FIG. 3 is a flowchart illustrating a method 200 of operating the anesthesia delivery system 100. The electronic processor 110 first receives an output signal from the neural sensor 105 when the neural sensor 105 is coupled to a patient (block 205). As discussed above, the output signal is indicative of neural activity of the patient. As also discussed above, the output signal from the neural sensor 105 may first undergo pre-processing. The capture of the output signal is shown as the raw neural signal in FIG. 2, which is directed to the preprocessing block 186. The electronic processor 110 (e.g., shown generally as the adaptive closed-loop controller 184 of FIG. 2) then accesses an estimator model 160, 165 from memory 115 and estimates a drug concentration of the patient using the estimator model 160, 165 (block 210). Specifically, the estimator 180 accesses the estimator model 160, 165 (or the three parametric models 130-155) to estimate the drug concentration of the patient. In particular, the drug concentration of the patient is estimated using a first model parameter (e.g., parameters $\theta_1(t-1)$, $\theta_2(t-1)$, $\theta_3(t-1)$), which is estimated during a previous cycle). In other words, the current drug concentration of the patient is estimated using previously estimated model parameters and/or a previously estimated drug concentration of the patient. The drug concentration of the patient includes both the brain drug concentration and the plasma drug concentration of the patient.

The electronic processor 110 (e.g., the estimator 180) also uses the estimator model 160, 165 to estimate an updated (or second) model parameter (block 215). The second model parameter is estimated based on the received output signal from the neural sensor 105. In some embodiments, the second model parameter is also based on the previously estimated model parameter and/or a previously estimated drug concentration. As shown in FIG. 2, the estimator 180 estimates the drug concentration of the patient and the model parameters and sends these estimates to the feedback controller 175. In the illustrated embodiment, the estimator 180 determines updated values for each of the three model parameters $\theta_1(t)$, $\theta_2(t)$, $\theta_3(t)$. In other embodiments, the estimator 180 may determine an updated value for only one or some of the three model parameters (e.g., only for $\theta_1(t)$).

The electronic processor 110 then updates a model parameter of the estimator model 160, 165 with the updated model parameter (block 220). In other words, the electronic processor 110 replaces the previously estimated model parameter with the updated model parameter. The electronic processor 110 then outputs control signals to the infusion pump 120 based on the estimated drug concentration of the patient (block 225). Upon receipt of the control signals, the infusion pump 120 operates to deliver the anesthetic drug according to the control signals and thereby maintain the patient at a target anesthetic state.

Figure 4:
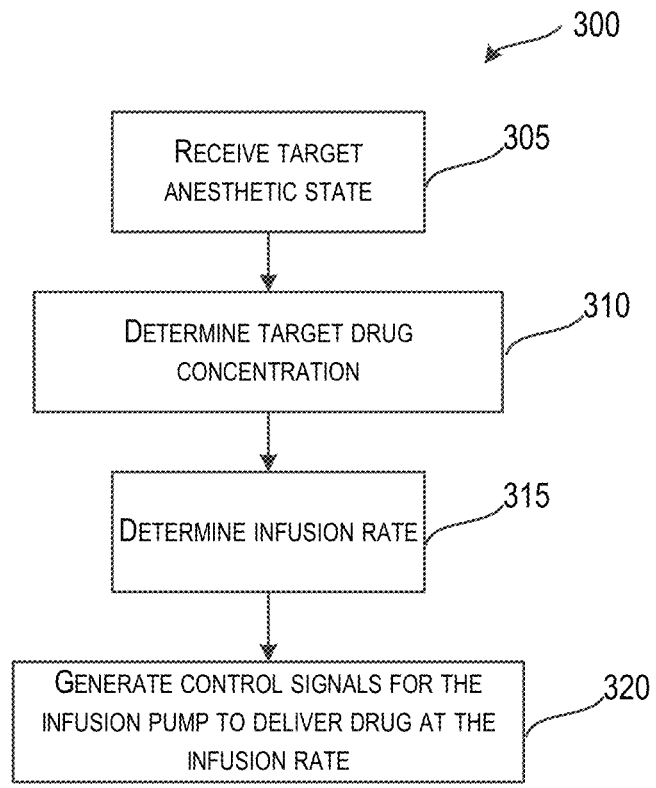
FIG. 4 is a flowchart illustrating a method of outputting control signals to an infusion pump of the anesthetic drug delivery control of FIG. 1.

FIG. 4 is a flowchart illustrating a method 300 of outputting the control signals to the infusion pump as described by block 225 of FIG. 3. First, the electronic processor 110 receives an indication of a target anesthetic state for the patient (block 305). FIG. 2 illustrates the communication of the target anesthetic state via the target anesthetic state block 190. The target anesthetic state may be accessed by both the feedback controller 175 and the estimator 180. The electronic processor 110 receives the indication via the input interface 117. The indication includes a target value of a neural signature corresponding to the target anesthetic state, as shown in the target anesthetic state block 190 of FIG. 2. As discussed above, different anesthetic states may use different neural signatures, and a given value for the neural signature indicates a precise level of anesthetic state. Notably, the value of the neural signature may include a time-varying function if, for example, the value of the neural signature changes over time. In one example, the electronic processor 110 may receive an indication that the target anesthetic state corresponds to a median frequency of 5 Hertz. Such an indication also informs the electronic processor 110 that the target anesthetic state is a level of unconsciousness under general anesthesia.

The electronic processor 110 then determines a target drug concentration of the patient based on the target anesthetic state (block 310). In particular, the electronic processor 110 determines the target drug concentration of the patient based on the target neural signature value. The electronic processor 110 may, in some embodiments, determine the target drug concentration by computing the inverse of the pharmacodynamic model 135, 150. The inverse of the pharmacodynamic model 135, 150 describes the relationship between the value of the neural signature and the drug concentration of a patient. The electronic processor 110 (e.g., the feedback controller 175) then proceeds to determine an infusion rate based on the target drug concentration (block 315). The electronic processor 110 determines an infusion rate by minimizing a cost function. In some embodiments, the cost function is stored within the infusion rate control model 170 and accessed by the feedback controller 175 (e.g., continuously in real-time). The cost function is defined by Equation 28 below:

$$J = \Sigma_{t=1}^{T}(x_e(t)-x^*)^2 + w_r(u_{t-1}-\bar{u})^2 + w_s(u_t-u_{t-1})^2 \qquad \text{Equation 28}$$

As shown in Equation 28, the cost function includes three terms: an error between the target drug concentration and the estimated drug concentration of the patient (e.g., $(x_e(t)-x^*)$), an error between a steady state infusion rate (e.g., $\bar{u}$) and a previous infusion rate (e.g., $u_{t-1}$), and an error between an optimal infusion rate and the previous infusion rate (e.g., $(u_t-u_{t-1})$). In particular, the error between the infusion rate and a previous infusion rate reduces the variability in the drug infusion rate with respect to previously administered drug infusion rates. Without accounting for this term in the cost function, the system 100 may be susceptible to noise and variabilities that would cause the infusion rate to constantly change.

In the illustrated embodiment, the electronic processor 110 minimizes the cost function of Equation 28 and finds that the infusion rate at time t is given by Equation 28:

$$u_t = -\tilde{L}\tilde{x}_t + u_{t-1} \qquad \text{Equation 29}$$

Where:

$$\tilde{x}_t = \left[x_c(t) - \frac{\hat{\theta}_2}{\hat{\theta}_1}x^*, \; x_e(t) - x^*, \; u_{t-1} - \frac{\hat{\theta}_2\hat{\theta}_3}{\hat{\theta}_1}x^*\right]'$$

$$\tilde{L} = (w_r + \tilde{B}'\tilde{P}\tilde{B})^{-1}\tilde{B}'\tilde{P}\tilde{A}$$

$$\tilde{P} = \tilde{S} + \tilde{A}'\tilde{P}\tilde{A} - \tilde{A}'\tilde{P}\tilde{B}(w_r + \tilde{B}'\tilde{P}\tilde{B})^{-1}\tilde{B}'\tilde{P}\tilde{A}$$

$$\tilde{A} = \begin{bmatrix} 1-\Delta(\hat{\theta}_1+\hat{\theta}_3) & \Delta\hat{\theta}_2 & \Delta \\ \Delta\hat{\theta}_1 & 1-\Delta\hat{\theta}_2 & 0 \\ 0 & 0 & 1 \end{bmatrix}, \; \tilde{B} = \begin{bmatrix} \Delta \\ 0 \\ 1 \end{bmatrix}$$

$$\tilde{S} = \begin{bmatrix} 0 & 0 & 0 \\ 0 & 1 & 0 \\ 0 & 0 & w_r \end{bmatrix}$$

Equation 30 and the equations defining the variables used in Equation 30 are stored in the infusion rate control model 170 stored in memory 115. The feedback controller 175 accesses the infusion rate control model 170 and determines the infusion rate using Equation 30. Therefore, the electronic processor 110 (e.g., the feedback controller 175) uses the estimation of the plasma drug concentration, the brain drug concentration, and the model parameters to determine the infusion rate. As shown in FIG. 2, the feedback controller 175 receives the target brain drug concentration, the estimated drug concentration(s) of the patient, and the estimated model parameters and outputs the drug infusion rate. Once the electronic processor 110 determines the infusion rate, the electronic processor 110 generates the control signals such that the infusion pump 120 delivers the anesthetic drug at the infusion rate (block 320). The electronic processor 110 then proceeds to outputting the control signals to the infusion pump 120 as described with respect to block 225 of FIG. 3.

Figure 5:
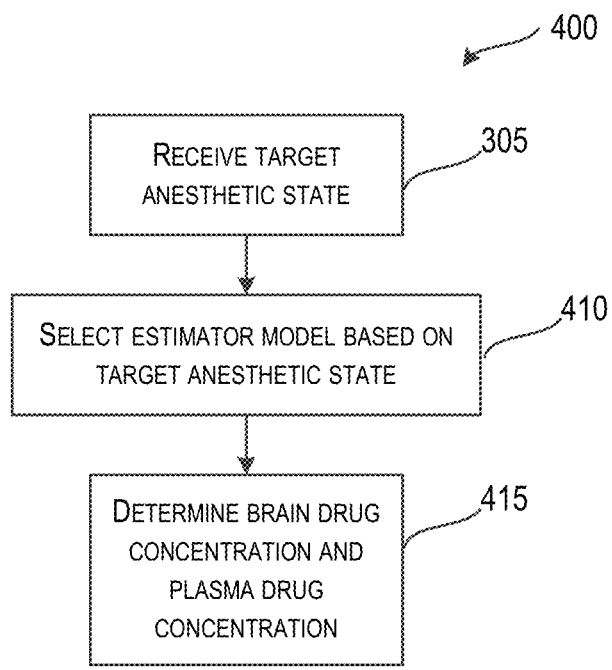
FIG. 5 is a flowchart illustrating a method of estimating the drug concentration of a patient.

FIG. 5 is a flowchart illustrating a method 400 of estimating the drug concentration of a patient as described with respect to block 210. The electronic processor 110 receives the indication of the target anesthetic state (block 305), as described with respect to FIG. 4 and the target anesthetic block 190 of FIG. 2. The electronic processor 110 (e.g., the estimator 180) determines, based on the indication of the target anesthetic state, a type of anesthetic state and an estimator model 160, 165 that corresponds to the target anesthetic state. The electronic processor 110 then selects, based on the target anesthetic state, an appropriate estimator model 160, 165 to estimate the drug concentration of the patient and the at least one model parameter (block 410). As discussed above, since the anesthesia delivery system 100 may be able to provide monitoring for different types of anesthetic states, the electronic processor 110 first selects which estimator model to use such that the selected estimator model provides adequate estimations of the drug concentration of the patient and the model parameter(s). For example, when the target anesthetic state is a first type anesthetic state (e.g., medically-induced coma), the electronic processor 110 selects the first estimator model 160. However, when the target anesthetic state is a second type of anesthetic state (e.g., unconsciousness), the electronic processor 110 selects the second estimator model 165. Then, based on the selected estimator model 160, 165, the electronic processor determines a brain drug concentration and a plasma drug concentration (block 415), as also described with respect to block 210 of FIG. 3.

Figure 6:
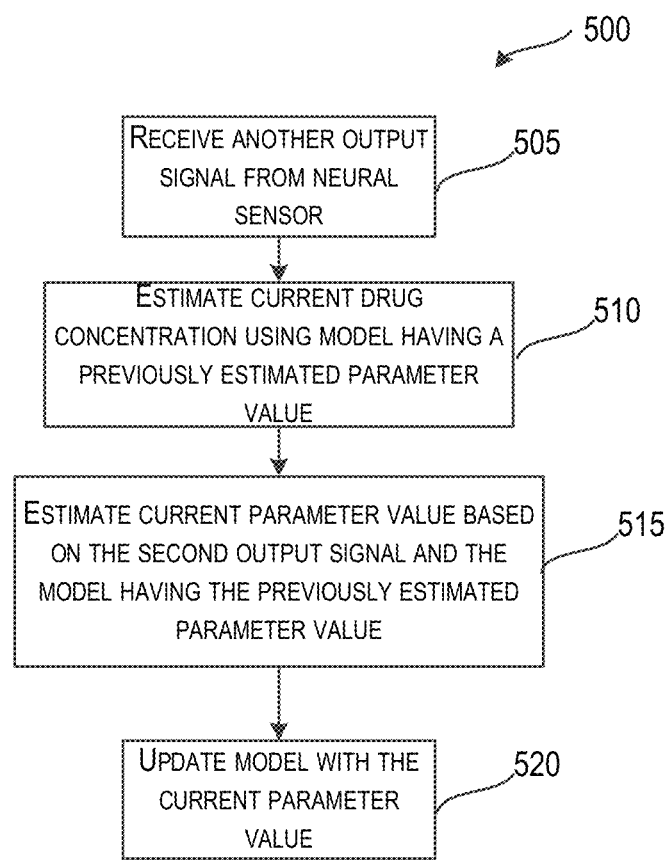
FIG. 6 is a flowchart illustrating a method of recursively updating the estimator models.

FIG. 6 is a flowchart illustrating a method 500 of recursively updating the estimator models 160, 165. Method 500 is described as a continuation of method 200 of FIG. 3 to illustrate the recursive nature of updating the model parameter(s). It is to be understood that the output signal from the neural sensor of block 205 is a first output signal (e.g., an output signal collected at time t). In method 500, while the infusion pump 120 is controlled by the electronic processor 110, the electronic processor 110 receives another output signal from the neural sensor 105 (block 505). The new output signal is received from the neural sensor at time t+1. As discussed above with respect to block 186 of FIG. 2, the output signals from the neural sensor 105 are pre-processed. The electronic processor 110 then proceeds to estimating a current drug concentration of the patient (block 510). For example, if the first drug concentration estimated in block 210 of FIG. 3 is estimated at time t, the second drug concentration estimated at block 510 is estimated at time t+1. The electronic processor 110 estimates the current drug concentration using the previously estimated parameter value (e.g., parameter value estimated at block 215 of FIG. 3). In other words, even though the second output signal is received at time t+1, the second drug concentration is based on the model parameter estimated at time t. Notably, the previously estimated parameter value referred to in block 510 has a different value than the parameter value used to estimate the first drug concentration in block 210 of FIG. 3. The electronic processor 110 also estimates a current parameter value (e.g., an updated or new model parameter value) based on the current output signal from the neural sensor 105 and the model having the previously estimated parameter value (block 515). The electronic processor 110 then updates the model with the current parameter value (e.g., replace the value of the second model parameter with the value of the third model parameter) at block 520. As discussed above, the anesthetic state of the patient changes the way in which the brain of the patient reacts to the injected drug. Therefore, by recursively updating the estimation of the drug concentration of the patient and the model parameters, the anesthesia delivery system 100 remains adaptable and accurate despite the time-varying nature of the pharmacodynamic and pharmacokinetic models.

The steady-state bias of the models 130-165 is reduced to ensure the accuracy of the models. Based on the stochastic models 130, 145, and in particular, the conditions required of the stochastic models 130, 145, the steady-state bias of the anesthesia delivery system 100 is derived as shown below by Equation 30:

$$\text{Bias} = \frac{x_e - x^*}{x^*} = (1+\delta_4)\frac{\hat{r}^{ss} - r}{r + \delta_3 + (r - \hat{r}^{ss})\delta_4} \quad \text{Equation 30}$$

Where $x_e = \lim_{t \to \infty} x_e(t)$ is the value of the brain drug concentration at steady state $\delta_3$ and $\delta_4$ are positive constants, r is the following ratio of the true unknown parameters $$r = \frac{\theta_2 \theta_3}{\theta_1}$$

and $\hat{r}^{ss}$ is defined as the following ratio computed from the estimated model parameters at steady state:

$$\hat{r}^{ss} = \lim_{t \to \infty} \frac{\hat{\theta}_2(t)\hat{\theta}_3(t)}{\hat{\theta}_1(t)} = \frac{\hat{\theta}_2^{ss}\hat{\theta}_3^{ss}}{\hat{\theta}_1^{ss}}$$

This steady state ratio is guaranteed to satisfy $\hat{r}^{ss} = r$, regardless of the initial values of the model parameters. Therefore, the bias of the adaptive system 100 is zero. The equations above show that the crucial condition to ensure zero steady-state bias for the system 100 is the correct estimation of the ratio r (i.e., a subspace of the true parameters). True ratio r can be different at different target levels. Under a non-adaptive system this ratio would remain the same after a system identification in which static parameter values are determined. However, under the adaptive system 100, the model parameters are continuously and recursively updated such that the ratio will update to $$\hat{r}^{ss} = \frac{\hat{\theta}_2(t)\hat{\theta}_3(t)}{\hat{\theta}_1(t)}.$$

Therefore, the construction of the models, in particular the stochastic models 130, 145, and the recursive updating of the model parameters, ensures that the estimated ratio tracks the true ratio r, and thereby ensures that the system achieves a zero steady-state bias.

Figure 7:
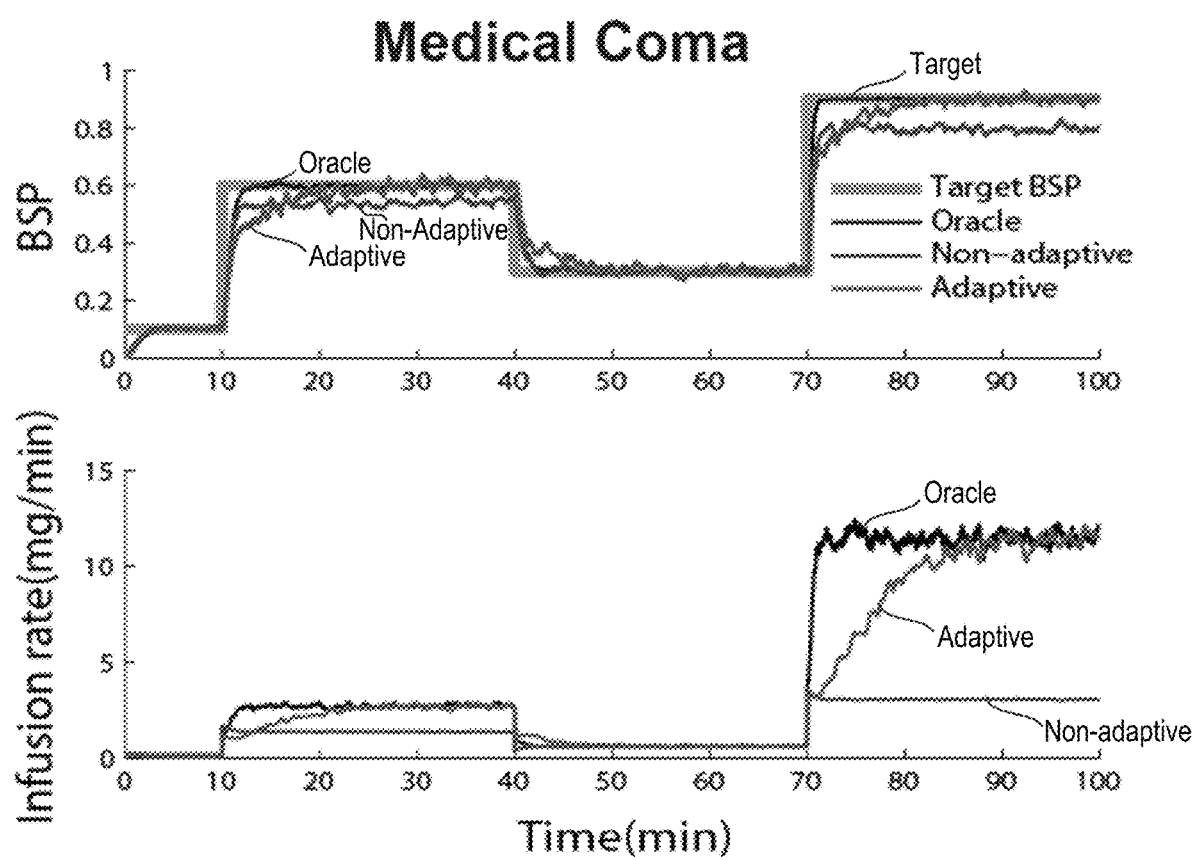
FIG. 7 are graphs illustrating an exemplary operation of the adaptive anesthetic drug delivery control for a first anesthetic state.

FIG. 7 are graphs illustrating an exemplary operation of the anesthetic drug delivery system 100 when the desired anesthetic state is a burst suppression under medically-induced coma. The top graph of FIG. 7 compares the target neural signature associated with the burst suppression under medically-induced coma (e.g., the burst suppression probability values), the neural signature calculated from a theoretical ideal system (referred to as Oracle), the neural signature calculated by the adaptive anesthesia delivery system 100, and the neural signature calculated by a non-adaptive anesthesia delivery system (referred to as non-adaptive). The theoretical ideal system (Oracle) represents an ideal control that uses the true values for the model parameters. The non-adaptive delivery system represents one that performs a system identification session and fixes the system parameters to those parameters determined during the system identification session, such that the system parameters do not change during operation.

The bottom graph of FIG. 7 illustrates the infusion rate over time for the theoretically ideal system (Oracle), the adaptive anesthesia delivery system 100, and the non-adaptive delivery system. As shown by both graphs of FIG. 7, the adaptive anesthesia delivery system 100 follows both the neural signature values and the infusion rate closer to the Oracle system when compared to the non-adaptive anesthesia delivery system. In other words, there is a significant improvement in the accuracy with which the target anesthetic state is maintained for a patient when the adaptive anesthesia delivery system 100 is used instead of the non-adaptive anesthesia delivery system.

Figure 8:
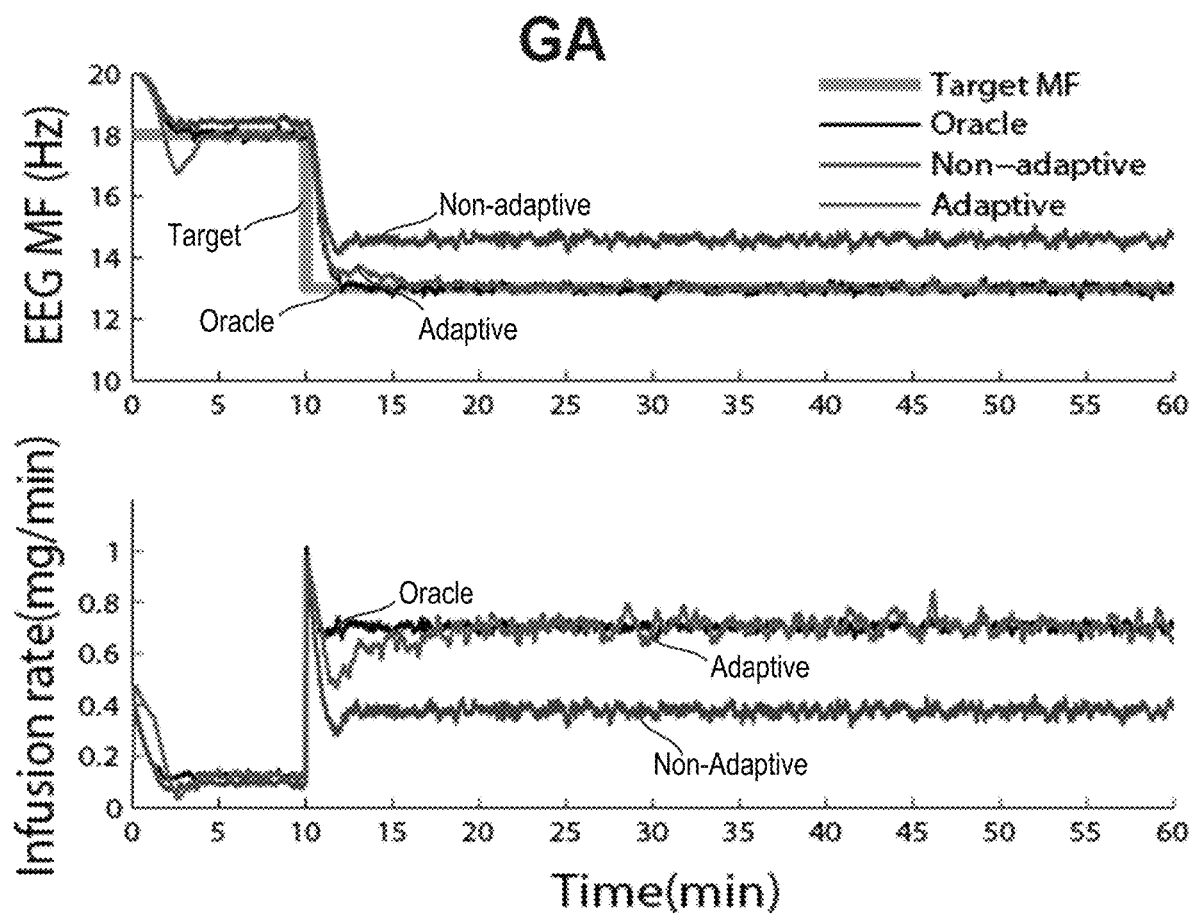
FIG. 8 are graphs illustrating an exemplary operation of the adaptive anesthetic drug delivery control for a second anesthetic state.

FIG. 8 are graphs illustrating an exemplary operation of the anesthetic drug delivery system 100 when the desired anesthetic state is control of unconsciousness under general anesthesia. The top graph of FIG. 8 compares the target neural signature values associated with the burst suppression under medically-induced coma (e.g., the median frequency values), the neural signature calculated from the theoretical ideal system (referred to as Oracle), the neural signature calculated by the adaptive anesthesia delivery system 100, and the neural signature calculated by a non-adaptive anesthesia delivery system (referred to as non-adaptive), similar to the top graph shown in FIG. 7.

The bottom graph of FIG. 8 illustrates the infusion rate over time for the theoretically ideal system (Oracle), the adaptive anesthesia delivery system 100, and the non-adaptive delivery system. As shown by both graphs of FIG. 8, the adaptive anesthesia delivery system 100 follows both the neural signature values and the infusion rate closer to the Oracle system when compared to the non-adaptive anesthesia delivery system. In other words, there is a significant improvement in the accuracy with which the target anesthetic state is maintained for a patient when the adaptive anesthesia delivery system 100 is used instead of the non-adaptive anesthesia delivery system.

Simulations were designed, informed by previous rodent experiments, to examine the performance of the proposed adaptive system 100 for medically-induced coma and its generalizability to general anesthesia. Simulation validation allows generalizability to be tested, which is difficult experimentally as it requires two completely different animal models: one for medical coma and one for general anesthesia. In what follows, control of medical coma is referred to as the BSP experiment and control of general anesthesia is referred to as the MF experiment. As an objective of an adaptive controller is to account for time-variation, non-stationarity, and noise, all these were incorporated in the simulations. In particular, the parameters for the pharmacokinetic model are time-varying, unknown, and noisy. The observations are also noisy because we use stochastic observation models. We simulate the true time-varying, uncertain, and noisy underlying drug dynamics as:

$$x_t = A_{t-1} x_{t-1} + B u_{t-1} + v_t;\qquad \text{Equation 32}$$

where $A_t$ and $B$ are in the same form as in Equation 3, and $v_t$ is a stochastic white Gaussian noise sequence with covariance matrix $V_M = 0{:}001 \times I_2$. To show that the adaptive controller can account for time-variation and noise, we assume that the time-varying system parameters $\theta_1(t)$, $\theta_2(t)$, $\theta_3(t)$ are changing linearly with both the brain and central drug concentrations, i.e., $x_e(t)$ and $x_c(t)$ at each time step and are noisy, i.e., $$\theta_1(t) = (1 + a_1 x_e(t) + b_1 x_c(t)) \theta_1^0, \qquad (33)$$

$$\theta_2(t) = (1 + a_2 x_e(t) + b_2 x_c(t)) \theta_2^0, \qquad (34)$$

$$\theta_3(t) = (1 + a_3 x_e(t) + b_3 x_c(t)) \theta_3^0, \qquad (35)$$

where $\theta_1(t)$, $\theta_2(t)$, $\theta_3(t)$ are the initial parameters at the beginning of the experiment, and $a_1$, $a_2$, $a_3$, $b_1$, $b_2$ and $b_3$ are noisy parameters. In each experiment, we choose $\theta_1(t)$, $\theta_2(t)$, $\theta_3(t)$ randomly from independent uniform distributions on $[0.5 \times 10^{-5}, 5 \times 10^{-5}]$, $[0.5 \times 10^{-2}, 5 \times 10^{-2}]$, and $[0.5 \times 10^{-3}, 5 \times 10^{-3}]$, respectively. The noisy model parameters are set as: $a_1 = 4 + \in_1^e, a_2 = 4 + \in_2^e, a_3 = 4 + \in_3^e, b_1 = 0.0002 + \in_1^c, b_2 = 0.0002 + \in_2^c, b_3 = 0.0002 + \in_3^c$, where in each experiment $\in_1^e, \in_2^e, \in_3^e$ independent model noises drawn from uniform distributions on $[-2;2]$, and $\in_1^c, \in_2^c, \in_3^c$ are independent model noises drawn from uniform distributions on $[0.0001, 0.0001]$. These ranges are chosen to give system parameters that are compatible with past data collected in a BSP control experiment in a rodent model. It is important to note that this parameter dynamics model, which also incorporates adequate uncertainty, merely serves to verify the architecture's performance. The proposed closed-loop system is general and applies to any other parameter dynamics as well.

Next, we specify the parameters in the stochastic models of Equations 16 and 22, and the pharmacodynamic models (hereinafter referred to as PD or PD models) of Equations 17 and 23. In Equation 16, we choose $N=10$ to be consistent with our prior work [11]. In Equation 22, we could approximate the value of $\sigma$ by the variance of the observed EEG MF when no anesthetic drug is being administered. Here, without loss of generality, we set $\sigma = 1$. Finally, for the PD model, Equation 17 does not require any parameter specification; for equation 23, we choose $E_0 = 20$ Hz and $E_{max} = 10$ Hz. As $x_e(t)$ is only a virtual measure of the brain concentration (through re-quantification of the neural signature $s(t)$), the value of $c_0$ is user's choice and is set to 1 mg here. $\gamma$ is chosen as 2 according to a previous study of methohexital anesthesia.

The above models provide a simulated test bench (they simulate the "subject", "neural signal recording system" and "preprocessing" blocks in FIG. 2). In the design of the closed-loop system, we assume we do not know the true pharmacokinetic model (hereinafter referred to as PK model or PK); indeed, we use this PK uncertainty and time-variation to summarize the non-stationarity and time-variations in the closed-loop system. We test the following systems: (i) the proposed adaptive system, (ii) a non-adaptive system, (iii) an oracle (unrealizable) system that knows the exact underlying parameters (33)-(35) above and hence provides us with the best performance possible by any closed-loop system, and (iv) an adaptive system without the infusion rate variation penalty $E_{t-1}^T w_s (u_t - u_{t-1})^2$ in the controller design of Equation 28, which does not enforce small variations in the infusion rates. We term this system as "adaptive without variation penalty" to distinguish it from the adaptive system.

The non-adaptive system needs a carefully designed offline system-identification session to estimate the model parameters. The simulated identification experiment lasts for 10 mins. The open-loop input $u_t$ is set as a bolus lasting for 1 min, i.e., $u_t = 1{:}8$ mg=min; $t \in [10 \text{ s}; 70 \text{ s}]$ and 0 elsewhere. For both GA and medical coma, we simulate two system-identification experiments. In one experiment, we take the observation as the true $x_e(t)$; this allows us to find the absolute best performance possible by a non-adaptive control system. In the other experiment, we consider a more realistic scenario where $x_e(t)$ needs to be estimated from the EEG observations $y_t$. We then apply the prediction error method (PEM) to estimate a set of constant parameters in both cases.

The adaptive estimator needs to choose initial values for the model parameters. We assume that the adaptive estimator has no initial knowledge of the system parameters and hence picks them randomly from independent uniform distributions on $[10^{-5}; 10^{-4}]$, $[10^{-2}; 10^{-1}]$ and $[10^{-3}; 10^{-2}]$, respectively, again based on our previous study on a rodent model. One free parameter in the estimator is Q, which we set as $Q = 0{:}00003 \times I_5$ across all experiments. To apply the controller, we set $w_r = 0{:}005$ and $w_s = 0{:}25$ across all experiments. These parameters are selected empirically for desired system response.

In addition, we run two more simulations to test the robustness of the adaptive algorithm with respect to two special scenarios that could happen in practice. First, there is evidence that even at a fixed anesthetic concentration, e.g., a fixed BSP level in medical coma, abrupt changes in neuronal activity happen. This might have led to the fact that in current depth-of-anesthesia monitors, occasional large jumps can happen with no apparent stimulation or change in anesthesia level. Abrupt change is a special case of non-stationarity and in our framework, we model this phenomena as an abrupt change of the PK model parameters. In this case, we simulate a scenario where we have maintained a constant level of BSP, e.g., 0.7, for a while before an abrupt change of the PK model parameters. During the initial maintenance phase, the PK model parameters, i.e., $\theta_1(t)$, $\theta_2(t)$, $\theta_3(t)$ are modelled as constants randomly selected from $[0.5 \times 10^{-5}, 5 \times 10^{-5}]$, $[0.5 \times 10^{-2}, 5 \times 10^{-2}]$, $[0.5 \times 10^{-3}, 5 \times 10^{-3}]$, respectively. An abrupt change of the PK model parameters then happens after 15 mins of maintenance, when $\theta_1(t)$, $\theta_2(t)$, $\theta_3(t)$ change to another constant value randomly selected from $[0.5 \times 10^{-5}, 5 \times 10^{-5}]$, $[0.5 \times 10^{-2}, 5 \times 10^{-2}]$, $[0.5 \times 10^{-3}, 5 \times 10^{-3}]$, respectively. We then compare the oracle system, adaptive system and non-adaptive system to investigate their responses to the abrupt change, and to examine if they can still maintain the same fixed level of BSP after the abrupt change of PK model parameters. In the simulations, the oracle system knows the true values of PK parameters; the non-adaptive system knows the true PK parameters only before the abrupt change, but does not adapt them after the abrupt change; the adaptive system uses random initial PK parameters and adapts PK parameters at every time step.

Second, hysteresis in dose-response characteristics of volatile agents such as halothane and isoflurane, have been found between the induction phase and emergence phase in flies and rats. In addition, this hysteresis cannot be simply explained by a difference of the PK models during induction and emergence. Therefore, this indicates that the PD model parameters can also be time-varying, and can influence the control performance. While in our framework we have assumed a time-invariant PD model, and have summarized all time-variations in the PK model parameters, it is essential to show the robustness of our adaptive system to time-variations in both PK and PD. In this case, we simulate a scenario for MF control in GA, where in addition to time-varying PK model parameters (as constructed in (33) to (35)), two PD model parameters in Equation 23, i.e., $C_0$ and $\gamma$, are also changing over time as follows:

$$C_0(t) = (1 + a_1 x_e(t) + b_1 x_c(t)) \times C_0^{nomial}, \tag{36}$$

$$\gamma(t) = (1 + a_2 x_e(t) + b_2 x_c(t)) \times \gamma^{nomial}, \tag{37}$$

where $C_0^{nomial} = 1$ mg, and $\gamma^{nomial} = 2$ as have been set in previous simulations. We again compare the oracle system, adaptive system and non-adaptive system with this additional PD time-variation. The oracle system knows the true PK and PD parameters; the non-adaptive system uses system-identification to determine PK parameters and uses $C_0^{nomial}$ and $\gamma^{nomial}$ in the PD model; the adaptive system uses random initial values of PK parameters, and uses $C_0^{nomial}$ and $\gamma^{nomial}$ in the PD model. We note that the proposed adaptive system is designed only to adapt the PK parameters but not the PD parameters; all time-variations, including those in PD parameters, are summarized in the time-varying PK parameters.

Here we present the performance metrics used to examine our results. We first characterize the system-identification performance of the non-adaptive system. As shown in section 2.6, the sufficient condition for the system to achieve zero steady-state bias is the correct estimation of the ratio $$\text{ratio} = \frac{\theta_2 \theta_3}{\theta_1}.$$

Hence we compute the estimation error of this ratio in system identification. Denoting the estimated ratio by $\hat{r}$, we calculate the relative estimation error (REE) of rt as $$REE = \frac{\hat{r} - \bar{r}}{\bar{r}} \times 100\%$$

where $$\bar{r} = \frac{1}{T} \sum_{t=1}^{T} r_t$$

is the mean of the true time-varying ratio rt. We denote the relative estimation error of rt using the true $x_e(t)$ by "REE ideal", and using the estimated $x_e(t)$ from $y_t$ by "REE realistic".

To characterize the performance of the closed-loop system at steady state, we compute the error between the target anesthetic state (represented by the neural signature) at each time, $s_t^*$, and the controlled anesthetic state, $\hat{s}_{t|t}$:

$$e_t = \hat{s}_{t|t} - s_t^*.$$

We use this error to calculate two standard metrics of performance. These metrics are the median prediction error (MDPE), $$MDPE = \text{median}\left(\frac{e_t}{s_t^*}\right) \times 100\%.$$

and the median absolute performance error (MDAPE)

$$MDAPE = \text{median}\left(\frac{|e_t|}{s_t^*}\right) \times 100\%.$$

The MDPE is a measure of bias at steady state and the MDAPE is a measure of normalized error. MDPE and MDAPE can also be calculated for rt to characterize the estimation performance of the crucial ratio rt in the adaptive system. In this case, in equations (40) and (41), we replace $\hat{s}_{t|t}$ with $$\hat{r}_t = \frac{\hat{\theta}_2(t) \hat{\theta}_3(t)}{\hat{\theta}_1(t)}$$

and $s_t^*$ with $r_t$

To characterize the drug infusion rate variations, we introduce the relative root mean-square error (RRMSE):

$$RRMSE = \frac{\sqrt{\frac{1}{T_2-T_1}\sum_{t=T_1}^{T_2}(u_t-u_{t-1})^2}}{\sqrt{\frac{1}{T_2-T_1}\sum_{t=T_1}^{T_2}u_t^2}} \times 100\%.$$

where T1 and T2 represent the starting time and ending time of a chosen steady-state level, respectively.

In this section, we present the simulation results. We show that: (1) despite performing offline system identification, non-adaptive control results in large error and bias in a time-varying environment as expected; this demonstrates that the bias observed in our rodent experiments at some levels could indeed be due to time-variation and non-stationarity, and hence that an adaptive controller needs to be designed to remove such bias; (2) the proposed adaptive system removes the bias and the need for a system-identification session; it tracks essential system non-stationarity (i.e., the time-varying ratio $$r = \frac{\theta_2\theta_3}{\theta_1})$$

to achieve precise control with low bias and error; (3) the adaptive controller further ensures small variations in drug infusion to achieve precise control with low bias and error; (3) the adaptive controller further ensures small variations in drug infusion rates at steady state; (4) the adaptive system is robust to abrupt changes of PK drug dynamics, as well as time-variations in PD. This presents the first adaptive controller of medically-induced coma; moreover, all results generalize to GA.

Biased control could be due to offline system identification in a time-varying non-stationary environment. In this section, we illustrate that the biased performance observed in rodent CLAD experiments could be due to the drawbacks of open-loop system identification of medical coma in a time-varying environment. More specifically, we show that offline system identification results in large estimation error of the time-varying crucial ratio $$r = \frac{\theta_2\theta_3}{\theta_1};$$

according to the analyses presented in section 2.6, this error will translate to large steady-state bias. We also show that this phenomenon holds for GA.

Figure 9:
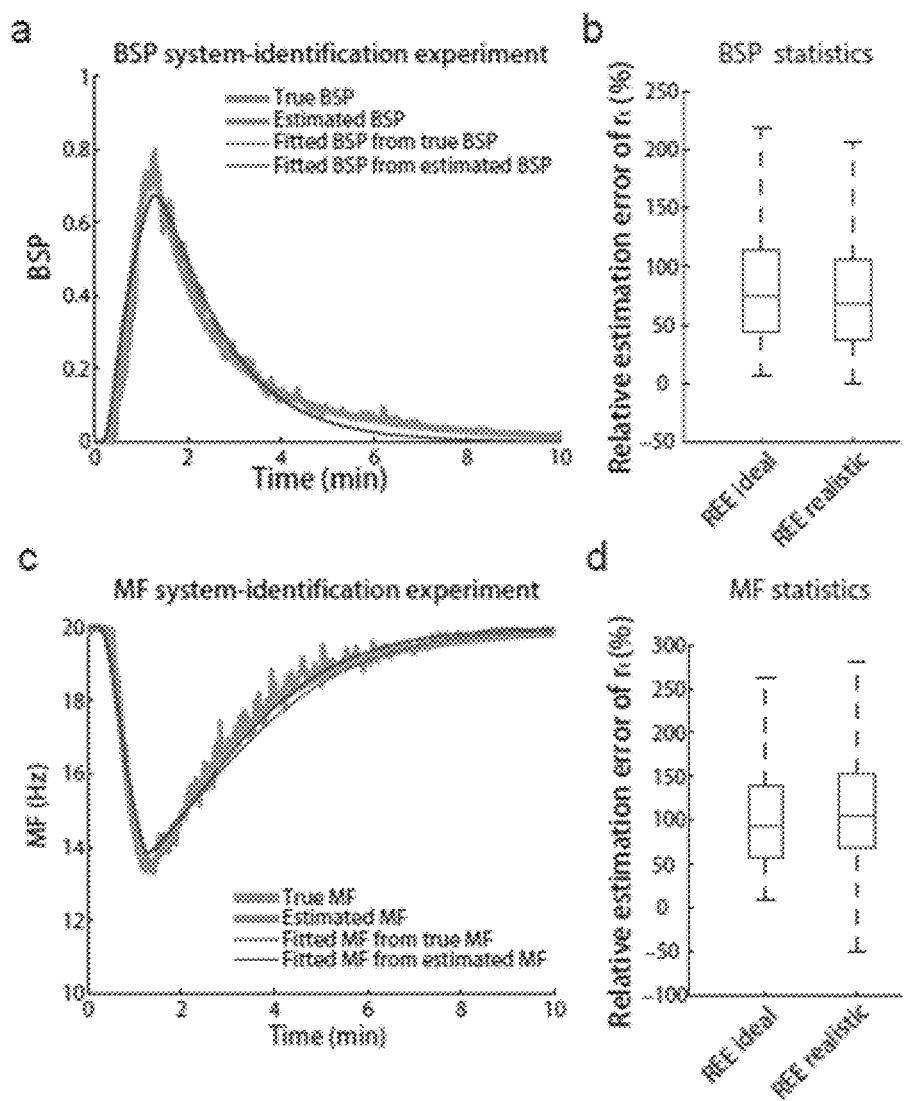
FIG. 9 are graphs illustrating that an offline system identification resulted in large estimation errors of the crucial ratio.
Figure 10:
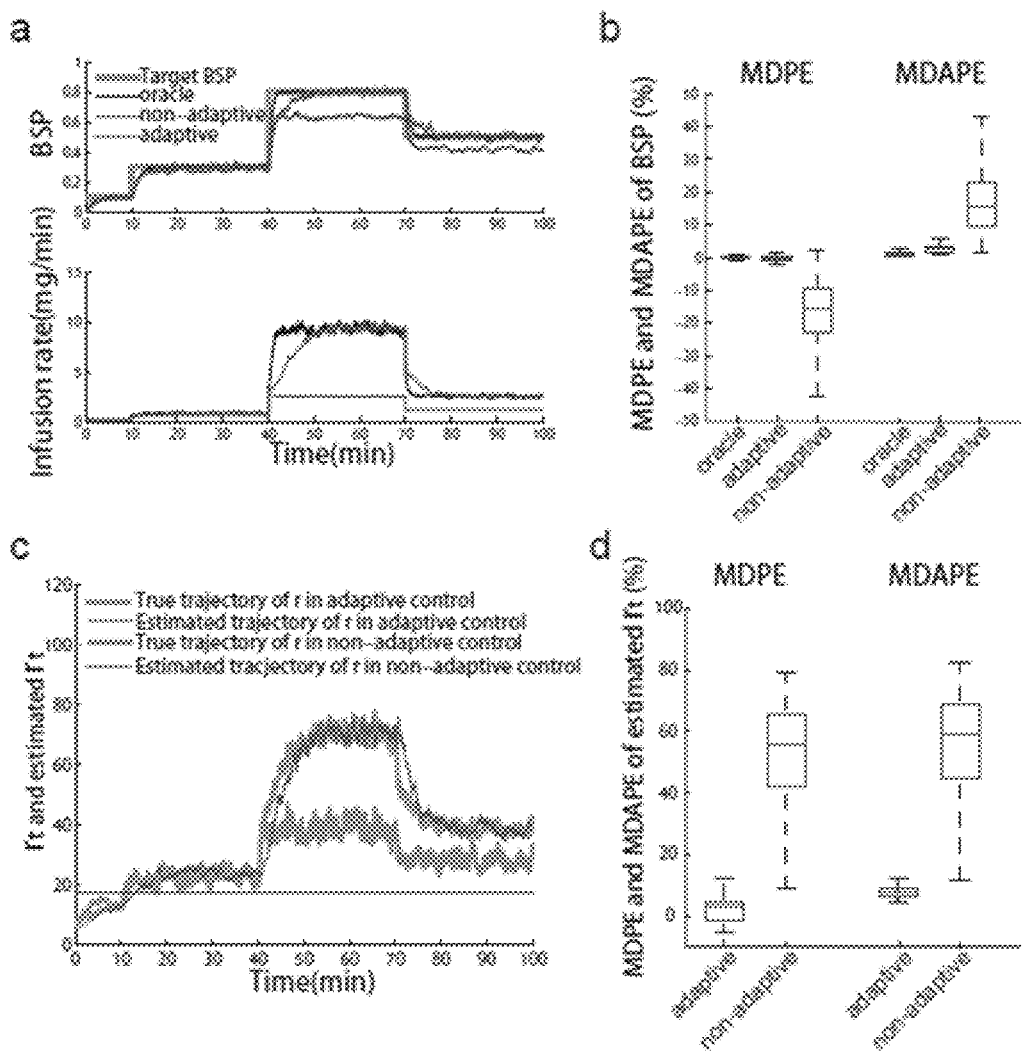
FIG. 10 are graphs showing details and results for simulations performed for the control of medical coma using the adaptive system of FIG. 1.

System identification only estimates constant system parameters even in a time-varying environment, and hence cannot capture the time-varying nature of the system. From both the BSP (FIG. 9(a,b)) and MF system-identification experiments (FIG. 9(c,d)), we see that whether the parameters were estimated directly using the true xe(t) or using the estimated xe(t) from yt, the relative error of estimating the crucial ratio ˆr was comparable and significantly above zero (in both cases, median REE ideal >70%, median REE realistic >65%). This indicates that even in the ideal case where xe(t) is known, offline system identification had large estimation errors of the timevarying parameter ratio rt. This predicts that by merely using the parameters estimated in a system-identification session, the system would result in a large bias in the controlled anesthetic state at steady state (as will be confirmed in experiments in FIGS. 10(a) and 11(a)). To make comparisons between non-adaptive and adaptive systems in the next sections, we use the estimated xe(t) in system identification. This is indeed also the realistic case that has been used in practice.

The adaptive system enables precise control in the presence of non-stationary time-varying drug dynamics. Here we show that the designed adaptive system could successfully eliminate biased performance and remove the need for a system-identification session. To assess our results, we compare the adaptive system with the oracle system and the non-adaptive system.

Adaptive control of medically-induced coma successfully removes the bias and the need for system-identification. We first ran a sample experiment to control BSP in medical coma for 100 mins (FIG. 10(a)). In the BSP experiment, the target was time-varying. It was set to 0.1 initially (0-10 mins) to let the parameters in the adaptive system converge (see Discussions). The target level then changed between 0.3, 0.8, and 0.5, and stayed at each level for 30 min. The controlled BSP trajectory in FIG. 10(a) shows that the adaptive system achieved precise control of BSP across different levels with low bias and error (averaged MDPE across levels −0.19%). Importantly, the adaptive performance was close to the baseline oracle performance (averaged MDPE 0.11%), demonstrating that the derived adaptive controller can effectively track system timevariation. As expected, the adaptive system performance was much better than the non-adaptive system, which had a large bias at steady state (averaged MDPE −12.51%). The infusion rates also illustrated consistent results. The infusion rates given by the adaptive system eventually converged to the optimal infusion rates given by the baseline oracle system. The non-adaptive system infusion rates were biased from optimal.

We then ran Monte Carlo experiments in which we simulated all 6 possible order permutations of 3 levels (0.3, 0.8 and 0.5). For each of the 6 permutations, we generated 100 independent underlying time-varying uncertain drug dynamics (see Equation 32) as stated in section 2.8. We then simulated closed-loop experiments for each underlying model and each control system. We then calculated the MDPE and MDAPE across all experiments and all levels. Results (FIG. 10(b)) show that the MDPE (bias) of the adaptive system was close to the baseline oracle performance (median MDPE, adaptive −0.32% v.s. oracle 0.15%). Also as expected, it was was 66 times smaller than the nonadaptive system (median MDPE, adaptive −0.32% v.s. nonadaptive −15.24%). Similar results held for MDAPE (error), where the median MDAPE of the adaptive system (2.31%) was close to the oracle performance (0.61%), and much smaller than the non-adaptive system (15.21%).

To show how the adaptive system achieves precise control in face of time-varying parameters, we examined how it tracked the time-varying ratio $$r = \frac{\theta_2\theta_3}{\theta_1},$$

whose precise estimation is the sufficient condition for zero steady state bias. The adaptive system responded to changes of this ratio promptly, and accurately tracked the time-varying ratio at steady state (FIG. 10(c)). Thus this explained why the adaptive algorithm had low bias at steady state. In contrast, the nonadaptive system resulted in large bias at steady state because it did not respond to changes of the ratio and could not track it. Note that the trajectory of true r is different in the adaptive and nonadaptive systems in FIG. 10 because system parameters depend on the real-time compartmental drug concentration values, which are different in the two systems. To further confirm this, we also calculated the MDPE and MDAPE for the steady-state estimates of rt across all experiments. The results (FIG. 10(d)) show that the adaptive system provided a much better estimate of this crucial ratio than the non-adaptive system (median MDPE, adaptive 1.48% v.s. non-adaptive 54.18%; median MDAPE, adaptive 4.48% v.s. non-adaptive 54.28%).

Another result worth noting is that the adaptive algorithm avoided overshoot and undershoot across all experiments (e.g., FIG. 10(a)). However, the controlled BSP trajectory in the adaptive system had a longer transition time than both the baseline and the non-adaptive system. This is because once the true system parameters changed, it took the estimated parameters some time to catch up. A detailed theoretical analysis of transition time and overshoot (undershoot) is beyond the scope of this paper and is the topic of our future work (see Discussion).

Figure 11:
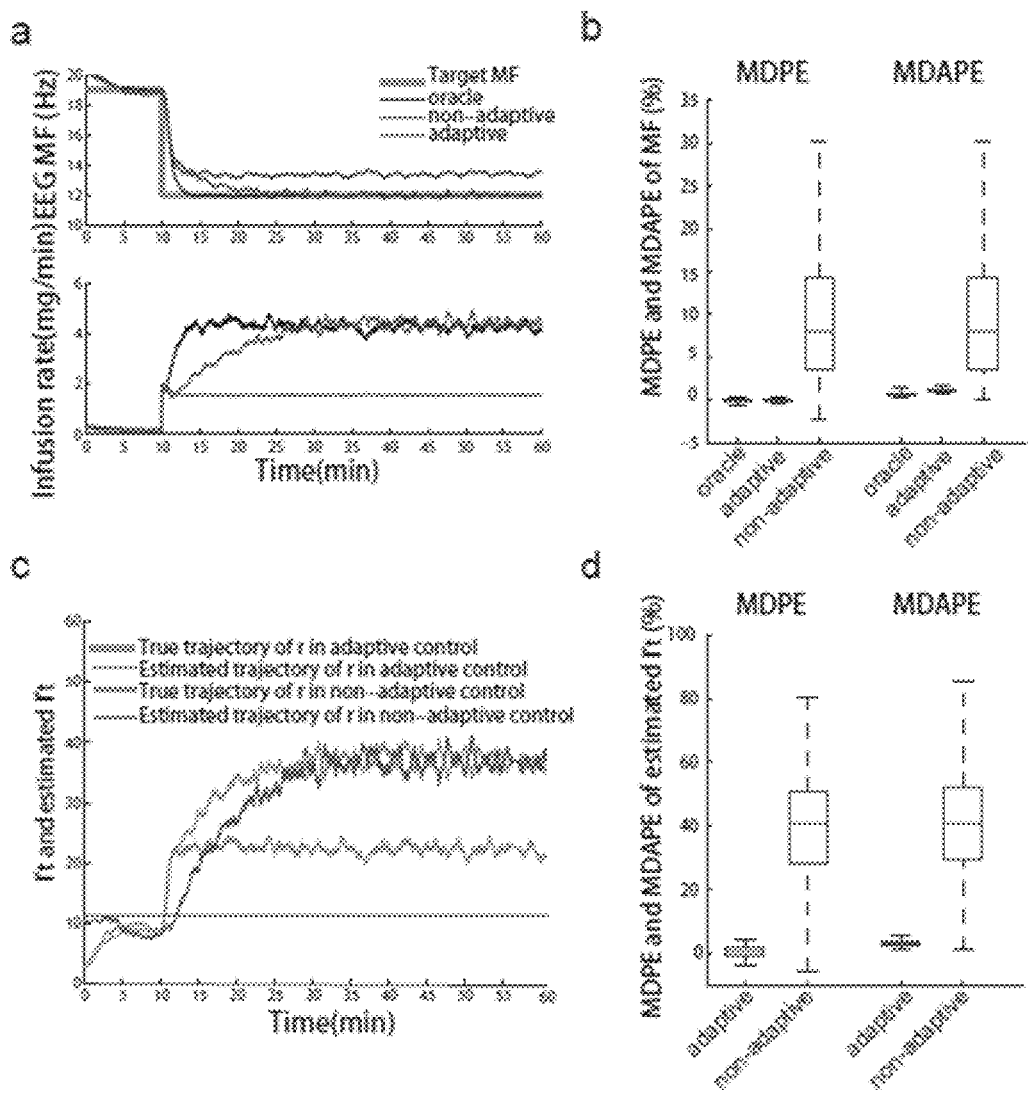
FIG. 11 are graphs showing details and results for simulations performed for the control of general anesthesia using the adaptive system of FIG. 1.

Adaptive control results generalize to other states of anesthesia. To show that our adaptive architecture is also generalizable, in addition to the BSP experiment in medical coma, we also evaluated it in the MF experiment in GA (FIG. 11). We ran the MF experiments for 60 mins. Here the target level was initially set to 19 Hz (0-10 mins) to let the parameters in the adaptive system converge. The target then changed to 12 Hz (10-60 mins). The performance of the oracle system, the adaptive system, and the nonadaptive system again followed the same trend as in the BSP experiment. The adaptive system tracked the target closely while the non-adaptive system had a large bias at steady state (FIG. 11(a)). The adaptive system also tracked the crucial ratio rt accurately while the non-adaptive system did not (FIG. 11(c)). We also ran Monte Carlo simulations, where we repeated the closed-loop control experiments 600 times on independently generated time-varying drug dynamics. The MDPE and MDAPE of MF and rt are shown in FIGS. 11(b) and 11(d). Compared with the non-adaptive system, the adaptive system again provided more accurate estimates of rt (median MDPE of rt, adaptive 0.33% v.s. non-adaptive 40.93%; median MDAPE of rt, adaptive 3.79% v.s. non-adaptive 41.83%), and thus resulted in precise control of the anesthetic state with small bias. The MDPE (bias) of the adaptive system was close to the oracle system (median MDPE, adaptive 0.03% v.s. oracle −0.01%), and again much smaller than the nonadaptive system (median MDPE, adaptive 0.03% v.s. nonadaptive 8.01%). Similar results held for MDAPE (error), where the median MDAPE of the adaptive system (0.53%) was close to the baseline oracle performance (0.32%) and 14 times smaller than the MDAPE of the non-adaptive system (8.01%). In addition, no overshoot occurred across all experiments.

Figure 12:
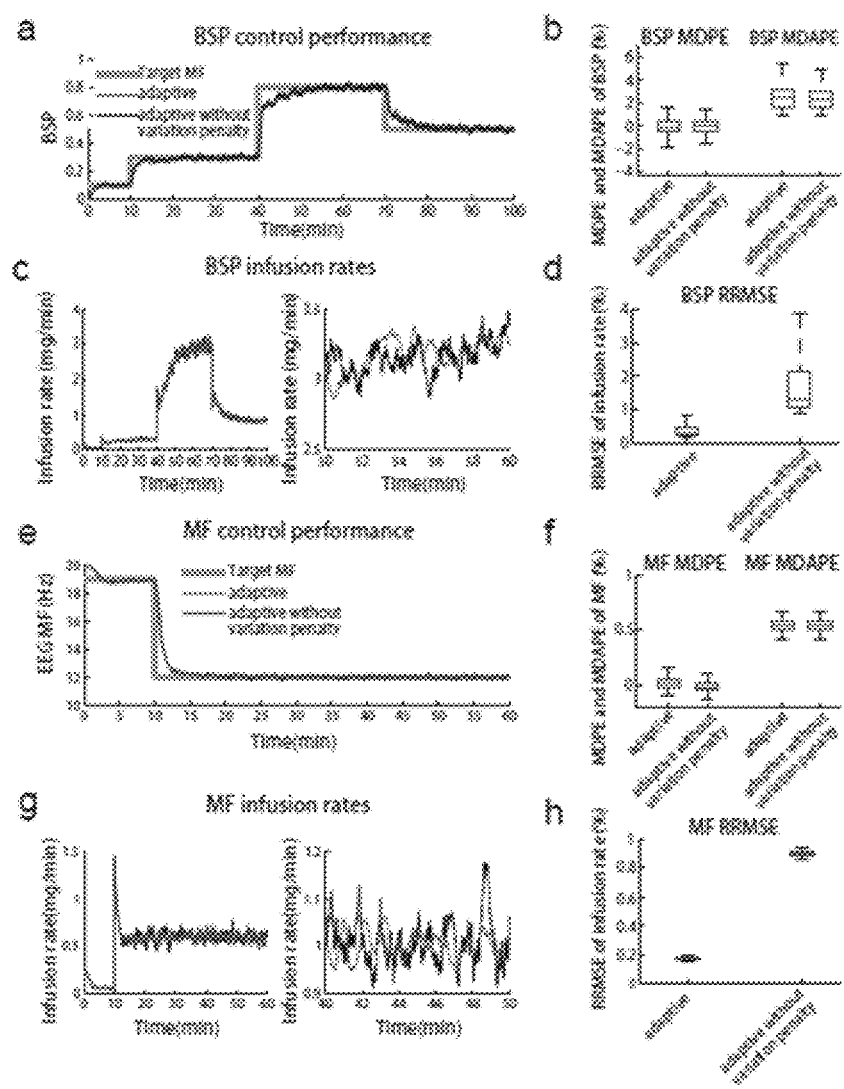
FIG. 12 are graphs illustrating that the adaptive system of FIG. 1 reduces infusion rates variations at steady state while achieving precise control.

The adaptive system enables small drug infusion rate variations at steady state. To show that we can address the third limitation posed in the Introduction, we also analyzed the infusion rate variations at steady state. We compared two systems (FIG. 12), the proposed adaptive controller that explicitly imposes small rate variations in the cost function (16), and the adaptive controller without variation penalty. We found that the adaptive system resulted in smaller infusion rate variations at steady state compared to the adaptive system without variation penalty, while at the same time achieving similar precise performance.

First, the controlled BSP and MF trajectories (FIGS. 12(a) and 12(e)) show that the two systems achieve similar precise control. To quantify this, we ran 500 Monte-Carlo experiments and calculated the MDPE and MDAPE of the controlled BSP and MF using both systems. The performance statistics (FIG. 12(b), 12(f)) show that the two systems had similar control bias and error. Second, the adaptive controller resulted in smaller variations in the infusion rates at steady state. Both FIG. 12(c) and FIG. 12(g) show that although infusion rates given by both systems converged to the same level, the infusion rate by the adaptive system was smoother than the adaptive system without variation penalty. To quantify the difference, we calculated the RRMSE of the infusion rates across all experiments. Compared with the the adaptive system without variation penalty (FIGS. 12(d) and 12(h)), the drug infusion rate variation of the adaptive system was almost 5 times smaller in both the BSP experiment (median RRMSE, adaptive 0.22% v.s. adaptive without variation penalty 1.31%) and the MF experiment (median RRMSE, adaptive 0.18% v.s. adaptive without variation penalty 0.91%). Together, these results show that the proposed CLAD architecture ensures small infusion rate variations at steady state without deteriorating the control precision of the anesthetic state.

The adaptive system was robust to abrupt changes in drug dynamics. As an important special case of non-stationarity, we tested the performance of the adaptive system in maintaining a fixed BSP level where PK model parameters made an unpredictable abrupt change during the maintenance. In a sample experiment with target BSP level 0.7, we see that when the abrupt change happened (FIG. 13(a), gray dotted line), the adaptive system responded actively to the change and after a short transition period (around 10 mins in this case), the controlled BSP level went back to 0.7 (FIG. 13(a), red). The control performance of the adaptive system was similar to the oracle controller; both the controlled BSP and infusion rate converged to the same level at steady state (FIG. 13(a), red v.s. black). In contrast, the nonadaptive system had large bias in controlling BSP after the abrupt change of the PK parameters (FIG. 13(a), blue v.s. green). Further, the adaptive system successfully tracked the parameter ratio $$r = \frac{\theta_2 \theta_3}{\theta_1}$$

Figure 13:
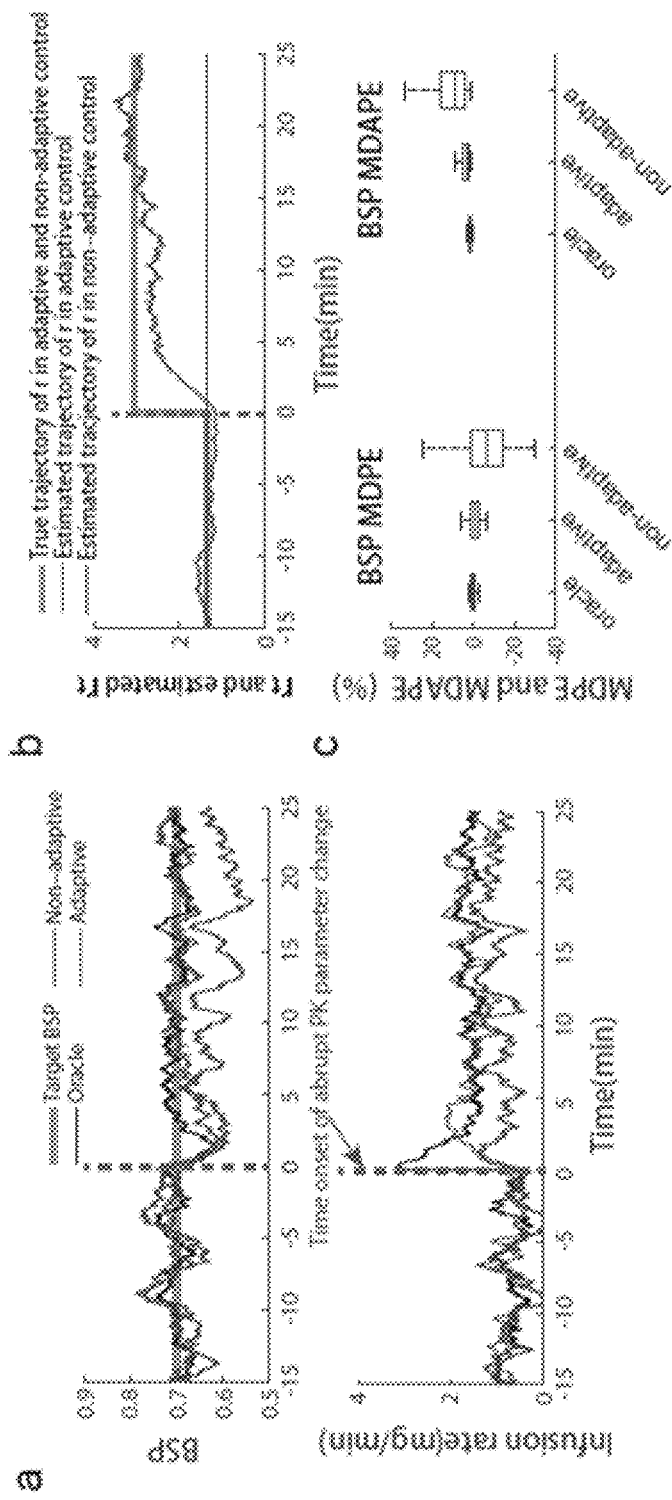
FIG. 13 are graphs illustrating the robustness of the adaptive system of FIG. 1 to abrupt changes in drug dynamics.

(FIG. 13(b), red v.s. green), again confirming the tracking of this ratio is crucial for the adaptive controller to reduce the tracking bias of BSP.

We further quantified the above observations in Monte-Carlo simulations where we simulated three different constant target BSP levels, 0.5, 0.7 and 0.9, each with 200 simulations with independently generated PK parameters and model noises. We calculated MDPE and MDAPE after the abrupt change at steady state (after a 15 mins transition period). The statistics show that MDPE of the adaptive system and oracle system was similar (FIG. 13(c), median MDPE: adaptive −0.56% v.s. oracle 0.18%), and was less than 110 of the non-adaptive system (FIG. 13(c), median MDPE: adaptive −0.56% v.s. non-adaptive 6.34%). In addition, the variance of MDPE of the adaptive system was only half of the non-adaptive system (FIG. 13(c), MDPE standard deviation: adaptive 5.77% v.s. non-adaptive 12.88%). Similar results hold for MDAPE, compared with the nonadaptive system, the adaptive system had smaller median MDAPE (FIG. 13(c), median MDAPE: adaptive 3.31% v.s. non-adaptive 9.33%), and smaller MDAPE variance (FIG. 13(c), MDAPE standard deviation: adaptive 4.73% v.s. non-adaptive 8.36%).

The above results show that the proposed adaptive system was robust to abrupt changes in drug dynamics that could happen in practical scenarios [39].

The adaptive system was robust to time-variations in both PK and PD. In the above simulations, we have only simulated time-varying PK models and have kept the PD model time-invariant. In this section, on top of time-varying PK models, we simulated time-varying PD models and tested the robustness of the adaptive system to time-variations in both PK and PD in MF control experiments.

Figure 14:
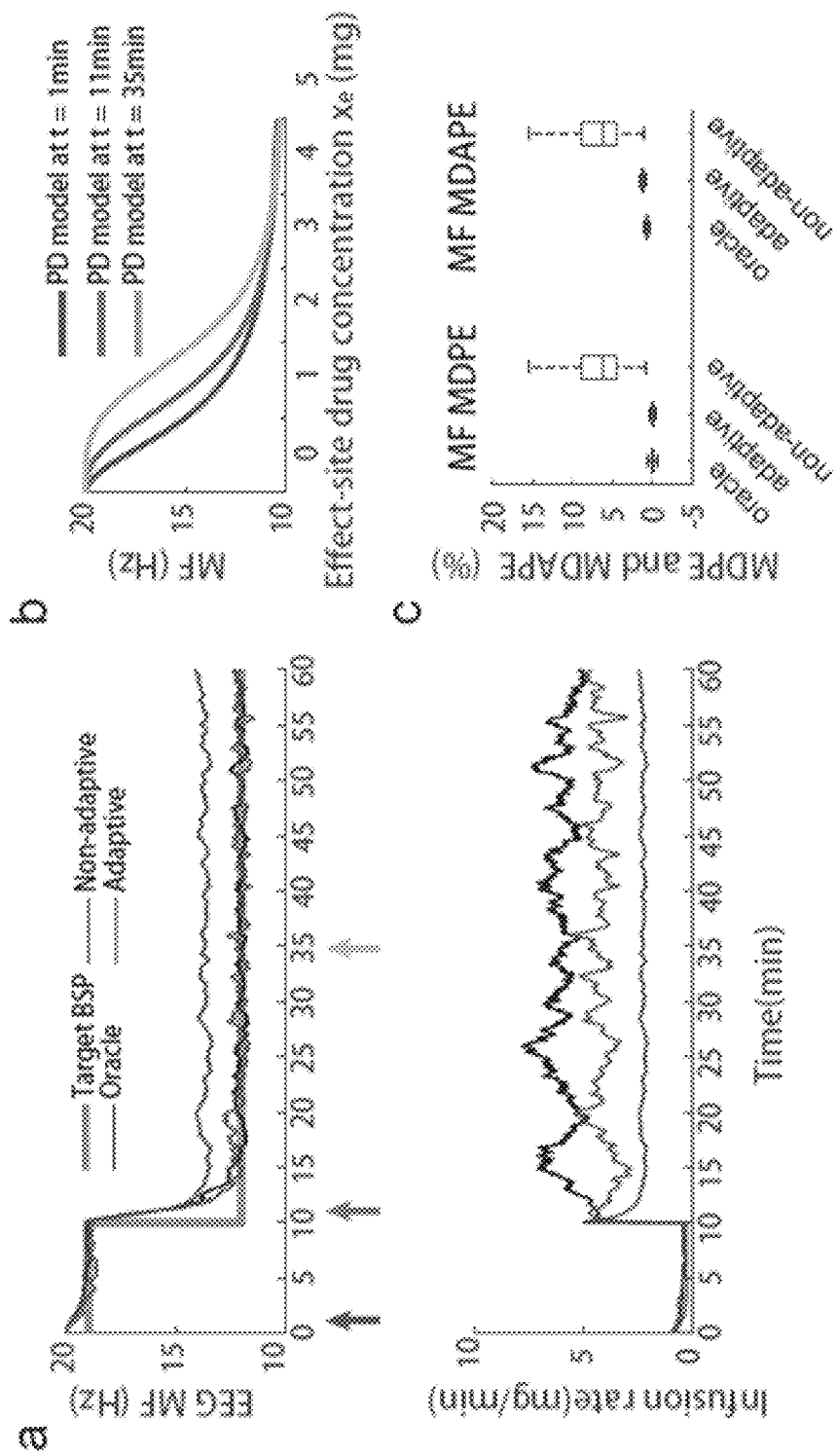
FIG. 14 are graphs illustrating the robustness of the adaptive system of FIG. 1 to time-variations in both a pharmacodynamics model and a pharmacokinetic model of the adaptive system of FIG. 1.

In an example simulation where PK and PD models were both non-stationary, the PD model changed with the drug concentration levels, showing significant different PD relationships at the beginning of the control, during transition and at the final steady state (FIG. 14(b)). In this scenario, the adaptive system stilled controlled MF to follow the target closely (FIG. 14(a), red v.s. green) with small bias and error (in this example, MDPE=0.13%, MDAPE=1.23%). The performance of the adaptive system was similar to the oracle system (FIG. 14(a), red v.s. black). Note that in this case, the infusion rate given by the adaptive system did not converge to that of the oracle system because the PD models were different in those two cases, meaning the save level of MF was caused by different levels of effect site drug concentration $x_e$, which led to different levels of steady-state infusion rates. In contrast, the non-adaptive system again resulted in biased control (FIG. 14(a), blue v.s. black) because it could track neither the PD time-variations nor the PK time-variations.

We then quantified the above observations in Monte-Carlo simulations. We ran 500 simulations with independent time-varying PK and PD model parameters. We compared MDPE and MDAPE of the oracle system, the adaptive system and the non-adaptive system at steady state. Results show that MDPE of the adaptive system and oracle system was similar (FIG. 14(c), median MDPE: adaptive −0.03% v.s. oracle −0.02%), and was less than 1/200 of the non-adaptive system (FIG. 14(c), median MDPE: adaptive −0.03% v.s. non-adaptive 6.03%). Similar results held for MDAPE, the adaptive system had much smaller MDAPE than the non-adaptive system (FIG. 14(c), median MDAPE: adaptive 1.05% v.s. non-adaptive 6.03%).

These results were quite surprising because the derivation of the adaptive estimator and controller was based on time-varying PK models and time-invariant PD models, but the results show that the system was even robust to time-varying PD models. This indicates that the proposed adaptive estimation and control framework is generalizable to different kinds of time-variations, regardless of whether they origin from PK or PD. One possible explanation is that the simple form of the 2-D PK model allow robust design of estimation and control algorithms that can track various kinds of time-variations, even the time-variations in PD, by using a time-varying PK model as an effective vehicle.

Thus, the invention provides, among other things, an adaptive control system for determining an optimal anesthetic infusion rate.

What is claimed is:

1. A system for controlling a state of anesthesia of a patient, the system comprising:
   a neural sensor configured to be coupled to a patient and generate an output signal indicative of neural activity of the patient; and
   an electronic processor coupled to the neural sensor and to an infusion pump, the electronic processor configured to:
      receive the output signal from the neural sensor,
      estimate a drug concentration of the patient using an estimator model, wherein the estimator model is configured to determine an estimated drug concentration based on the output signal from the neural sensor using a previously determined value of at least one parameter of the estimator model,
      calculate an updated value of the at least one parameter of the estimator model based on the output signal from the neural sensor and the previously determined value of the at least one parameter of the estimator model,
      update the estimator model by replacing the previously determined value of the at least one parameter with the updated value of the at least one parameter, and
      output control signals to the infusion pump to deliver a drug, the output signals being based on the estimated drug concentration for the patient.

2. The system of claim 1, further comprising an input device coupled to the electronic processor, and wherein the electronic processor is configured to receive an indication of a target anesthetic state for the patient through the input device.

3. The system of claim 2, wherein the indication includes a value corresponding to a target neural signature, and wherein the electronic processor is configured to determine a target drug concentration of the patient based on the target neural signature.

4. The system of claim 2, wherein the electronic processor is configured to determine an infusion rate based on the target anesthetic state and the estimated drug concentration of the patient, and wherein the control signals control the infusion pump to deliver the drug at the infusion rate.

5. The system of claim 4, wherein the infusion rate changes over time based on the estimated drug concentration of the patient to achieve the target anesthetic state.

6. The system of claim 4, wherein the electronic processor minimizes a cost function to determine the infusion rate, wherein the cost function is based on a difference between the infusion rate and a previously administered infusion rate, such that minimizing the cost function reduces a variability in the infusion rate with respect to the previously administered infusion rate.

7. The system of claim 6, wherein the cost function is also based on a second difference between a target drug concentration and the estimated drug concentration of the patient, and on a third difference between a steady state infusion rate and the previously administered infusion rate.

8. The system of claim 2, wherein the estimator model is a first estimator model, and
   wherein the electronic processor is configured to
      estimate the drug concentration of the patient using the first estimator model when the target anesthetic state is a first anesthetic state, and
      estimate the drug concentration of the patient using a second estimator model when the target anesthetic state is a second anesthetic state, wherein the first anesthetic state is different from the second anesthetic state, and wherein the second estimator model is different from the first estimator model.

9. The system of claim 8, wherein the first anesthetic state includes unconsciousness under general anesthesia and wherein the second anesthetic state includes medically-induced coma.

10. The system of claim 1, wherein the drug concentration includes a brain drug concentration and a central plasma drug concentration for the patient.

11. The system of claim 1, wherein the at least one parameter of the estimator model includes at least one selected from a group consisting of a drug flow rate from a central plasma to a brain of the patient, a drug flow rate out of the brain to the central plasma of the patient, and a rate of elimination of the drug.

12. The system of claim 1, wherein a construction of the estimator model ensures the system achieves a zero steady-state bias by accurately estimating a ratio of a first quantity to a drug flow rate from a central plasma to a brain of the patient, the first quantity being defined by a product of a drug flow rate out of the brain to the central plasma and a rate of elimination of the drug.

13. The system of claim 1, wherein the electronic processor is configured to estimate a ratio of a first quantity to a drug flow rate from a central plasma to a brain of the patient, the first quantity being defined by a product of a drug flow rate out of the brain to the central plasma and a rate of elimination of the drug, and wherein an accurate estimation of the ratio achieves a zero steady-state bias for the system.

14. The system of claim 1, wherein the system estimates a ratio of a first quantity to a drug flow rate from a central plasma to a brain of the patient, the first quantity being defined by a product of a drug flow rate out of the brain to the central plasma and a rate of elimination of the drug, and achieves a zero steady-state bias by the estimation of the ratio.

15. A system for controlling a state of anesthesia for a patient, the system comprising:
a controller configured to provide
an estimator configured to
receive pre-processed neural signals of the patient from a neural signal recording system,
recursively generate, by using a set of models, an estimate of a brain drug concentration of the patient and an updated value of an adaptable model parameter,
wherein the set of models includes
a first model relating the pre-processed neural signal with a value of a neural signature based on a pre-determined value of the adaptable model parameter,
a second model relating the brain drug concentration of the patient with the value of the neural signature based on the pre-determined value of the adaptable model parameter, and
a third model relating a drug infusion rate with the drug concentration based on a pre-determined value of the adaptable model parameter, and
periodically send the estimate of the brain drug concentration of the patient and the updated value of the adaptable model parameter to a feedback controller, and
the feedback controller configured to
periodically receive the estimate of the brain drug concentration of the patient and the updated value of the adaptable model parameter, and
periodically adjust an infusion rate of an anesthetic to be administered to the patient based on a target anesthetic state, the estimate of the brain drug concentration, and the updated value of the adaptable model parameter.

16. The system of claim 15, wherein the feedback controller adjusts the infusion rate by minimizing a cost function, based on a difference between a target brain drug concentration and the estimated brain drug concentration, a difference between a steady state infusion rate and the previously administered infusion rate, and on a difference between the infusion rate and a previously administered infusion rate.

17. The system of claim 15, wherein the estimator is further configured to recursively estimate a plasma drug concentration of the patient based on the first model, the second model, and the third model.

18. The system of claim 15, wherein the third model is a two-compartment model including the adaptable model parameter.

19. The system of claim 18, wherein the adaptable model parameter includes at least one selected from a group consisting of a drug flow rate from a central plasma to a brain of the user, a drug flow rate from the brain to the central plasma of the user, and a drug elimination rate.

20. The system of claim 15, wherein the first model, the second model, and the third model are associated with control of a first anesthetic state and wherein the system includes a fourth model, a fifth model, and a sixth model associated with control of a second, different, anesthetic state.

21. A method of controlling a state of anesthesia for a patient, the method comprising:
receiving a signal from a neural sensor, the signal indicative of neural activity of the patient;
estimating, with an electronic processor, a current brain drug concentration of the patient using an estimator model configured to determine an estimated value of the current brain drug concentration based on the neural activity of the patient and at least one parameter of the estimator model;
recursively updating the estimator model by replacing a previously determined value of the at least one parameter with an updated value of the at least one parameter based on the signal indicative of neural activity;
calculating, with the electronic processor, an infusion rate based on the estimated current brain drug concentration of the patient, the updated value of the at least one parameter of the estimator model, and a target anesthetic state of the patient,
wherein the infusion rate changes over time based on recursive estimates of the brain drug concentration of the patient and recursive updates of the at least one parameter of the estimator model; and
operating an infusion pump to deliver a drug based on the calculated infusion rate.

22. The method of claim 21, further comprising calculating the updated value of the at least one parameter based on one or more previously determined values of the at least one parameter.

23. The method of claim 20, wherein estimating the current brain drug concentration of the patient includes estimating the brain drug concentration of the patient using the estimator model with the previously determined value of the at least one parameter, wherein the previously determined value of the at least one parameter was calculated during a previous update of the estimator model.

24. The method of claim 20, further comprising estimating, with the electronic processor, a current plasma drug concentration of the patient.

* * * * *